(12) United States Patent
Heath et al.

(10) Patent No.: US 9,931,298 B2
(45) Date of Patent: Apr. 3, 2018

(54) LIPOSOME LOADING

(71) Applicant: COMFORT CARE FOR ANIMALS LLC, Middleton, WI (US)

(72) Inventors: Timothy D. Heath, Madison, WI (US); Lisa Ann Krugner-Higby, Belleville, WI (US); Amy Lautenbach, Cottage Grove, WI (US)

(73) Assignee: COMFORT CARE FOR ANIMALS LLC, Middleton, WI (US)

( * ) Notice: Subject to any disclaimer, the term of this patent is extended or adjusted under 35 U.S.C. 154(b) by 0 days.

(21) Appl. No.: 15/165,421

(22) Filed: May 26, 2016

(65) Prior Publication Data

US 2016/0346205 A1    Dec. 1, 2016

Related U.S. Application Data

(60) Provisional application No. 62/291,225, filed on Feb. 4, 2016, provisional application No. 62/166,223, filed on May 26, 2015.

(51) Int. Cl.
| | | |
|---|---|---|
| *A61K 9/127* | (2006.01) | |
| *A61K 31/47* | (2006.01) | |
| *A61K 31/4706* | (2006.01) | |
| *A61K 31/485* | (2006.01) | |
| *A61K 31/65* | (2006.01) | |

(52) U.S. Cl.
CPC ............ *A61K 9/1278* (2013.01); *A61K 9/127* (2013.01); *A61K 31/4706* (2013.01); *A61K 31/485* (2013.01); *A61K 31/65* (2013.01); *Y10S 977/773* (2013.01); *Y10S 977/906* (2013.01); *Y10S 977/907* (2013.01)

(58) Field of Classification Search
CPC ...................................................... A61K 9/127
See application file for complete search history.

(56) References Cited

U.S. PATENT DOCUMENTS

| | | | |
|---|---|---|---|
| 5,000,887 A | * | 3/1991 | Tenzel ................. A61K 9/1277 264/4.1 |
| 2006/0034908 A1 | | 2/2006 | Bhamidipati et al. |
| 2011/0024929 A1 | * | 2/2011 | Nakamura ........... A61K 9/1271 264/4.1 |
| 2011/0182980 A1 | * | 7/2011 | Yagi ..................... A61K 9/0019 424/450 |
| 2011/0250262 A1 | | 10/2011 | Shimizu et al. |
| 2014/0065204 A1 | | 3/2014 | Hayes et al. |

OTHER PUBLICATIONS

International Search Report, International Application No. PCT/US2016/034305, dated Oct. 26, 2016.

\* cited by examiner

*Primary Examiner* — Isaac Shomer
(74) *Attorney, Agent, or Firm* — Casimir Jones S.C.

(57) ABSTRACT

Provided herein is technology relating to incorporation of drugs into liposomes and particularly, but not exclusively, to methods for incorporating drugs into liposomes using a weak base and related compositions.

24 Claims, 16 Drawing Sheets

LIPOSOME LOADING

CROSS-REFERENCE TO RELATED APPLICATIONS

This application claims priority to U.S. Provisional Patent Application No. 62/166,223, filed May 26, 2015 and U.S. Provisional Patent Application No. 62/291,225, filed Feb. 4, 2016, the contents of each of which are incorporated by reference in their entirety.

STATEMENT REGARDING FEDERALLY SPONSORED RESEARCH OR DEVELOPMENT

This invention was made with government support under Grant No. 1R43DA037887-01 awarded by the National Institutes of Health. The government has certain rights in the invention.

FIELD

Provided herein is technology relating to incorporation of bioactive agents such as drugs into liposomes and particularly, but not exclusively, to methods and related compositions for incorporating bioactive agents into liposomes using a weak base.

BACKGROUND

Controlled-release drug formulations can be produced by incorporating drugs into liposomes. These formulations have many advantages including, e.g., extending the duration of a drug's effect following administration. Important considerations related to these technologies include the efficiency with which the drug is incorporated into liposomes and the release profile of the drug from the liposomes.

Some existing methods for incorporating drugs into liposomes employ passive aqueous capture. At best, this method incorporates only 50% of the drug into the liposomes and release rates after administration are very rapid. For example, previous data indicated that oxymorphone incorporation into dehydration-rehydration vesicles comprising egg phosphatidylcholine and cholesterol was 50% efficient and subsequent animal studies using these vesicles indicated that the release time was approximately 24 hours. In additional studies, incorporation of the drug into dehydration-rehydration vesicles comprising dipalmitoylphosphatidylcholine and cholesterol was only 7% efficient, although release times were more favorable at approximately 72 hours. In both cases, release rates were most rapid at early time points, resulting in high initial plasma concentrations of the drug.

Accordingly, technologies that combine efficient incorporation of drugs into liposomes with favorable release kinetics are needed.

SUMMARY

Gradient loading technologies provide an alternative to passive aqueous capture. In general, gradient loading methods improve the efficiency with which drugs are incorporated into liposomes. One illustrative example of this approach is the use of ammonium sulfate as a liposome loading agent. In particular, liposomes are prepared in an ammonium sulfate solution, which results in liposomes having ammonium sulfate in the intraliposomal space. Ammonium sulfate is also present in the extraliposomal space (e.g., in the bulk phase). The unincorporated ammonium sulfate in the bulk phase is eliminated by dialysis or other technique. Then, the drug is added to the washed liposomes comprising ammonium sulfate in the intraliposomal space. As the system equilibrates, the drug is loaded into the liposomes by the process of weak base exchange. This approach is 99% efficient for a drug such as doxorubicin, which precipitates as an insoluble sulfate after transport into the liposomes. However, loading is less efficient for most drugs because most drug sulfate salts are highly soluble in aqueous solutions. For example, previous studies have indicated that liposomes are loaded with opioid drugs (e.g., oxymorphone, hydromorphone, and buprenorphine) using the ammonium sulfate gradient technique at loading efficiencies of approximately 35%.

Despite such moderate loading, a benefit of ammonium sulfate loading is the improved release profile of opioids loaded into liposomes. In particular, therapeutic concentrations of opioids in the blood are maintained for 2 to 3 weeks after a single subcutaneous injection. However, as for passively loaded opioids, the early release rate is rapid, which results in undesirably high plasma concentrations for the first few days following injection.

Accordingly, provided herein is technology that provides highly efficient liposome loading with drugs and a reduced release rate (e.g., a reduced early release rate).

For example, some embodiments of the technology provide a liposome composition for preparing liposomes loaded with a bioactive agent, the composition comprising liposomes, the liposomes comprising a loading base in the intraliposomal space, the loading base having a pKa that is less than the pKa of the bioactive agent. In some embodiments, the compositions further comprise a loading medium in the extraliposomal space, the loading medium having a pH that is greater than the pKa of the loading base. In particular embodiments, the pH of the loading medium is controlled by using a pH buffer in the loading medium (e.g., in some embodiments the loading medium comprises a buffer; e.g., in some embodiments the extraliposomal space comprises a buffer). In some embodiments of the liposome composition for preparing liposomes, the concentration of the loading base in the intraliposomal space is greater than the concentration of the loading base in the extraliposomal space. In some embodiments, the (log P-pKa) of the loading base is greater than the (log P-pKa) of the bioactive agent.

The liposome compositions for preparing liposomes loaded with a bioactive agent are not limited in the loading base used. In some embodiments, the loading base is a weak base (e.g., the pKa of the loading base is less than 6, less than 5.5, less than 5, less than 4.5, less than 4, less than 3.5, less than 3, less than 2.5, or less than 2). In some embodiments, the loading base is a pyridine or pyridine derivative, e.g., a pyridinium, a 2-methoxy-pyridinium, a nicotinamide or a pyridazinium (e.g., a pyridinium ion, a 2-methoxy-pyridinium ion, or a pyridazinium ion; e.g., a pyridinium salt, a 2-methoxy-pyridinium salt, or a pyridazinium salt). In some embodiments, the log P of the loading base is less than 1.5, less than 1.0, less than 0.5, less than 0.0, or less than −0.5. The technology is not limited in the lipids used to prepare the liposomes. For example, in some embodiments the liposomes comprise phosphatidylcholine, e.g., a phosphatidylcholine selected from the group consisting of distearoylphosphatidylcholine, hydrogenated soy phosphatidylcholine, hydrogenated egg phosphatidylcholine, dipalmitoylphosphatidylcholine, dimyristoylphosphatidylcholine, and dielaidoylphosphatidylcholine. In some embodiments, the liposomes comprise a sphingomyelin; a neutral lipid; and/or an acidic phospholipid. Some embodiments of the technology are related to liposomes comprising a dipalmitoylphosphatidylcholine and, optionally, cholesterol.

In some embodiments, liposome compositions find use to prepare liposomes loaded with a bioactive agent. For example, some embodiments of the technology provide a composition comprising liposomes, a bioactive agent, and a loading base, the loading base having a pKa that is less than a pKa of the bioactive agent. In an exemplary embodiment of the compositions, the concentration of the bioactive agent in the intraliposomal space is greater than the concentration of the bioactive agent in the extraliposomal space and the concentration of the loading base in the intraliposomal space is less than the concentration of the loading base in the extraliposomal space. In some embodiments, the (log P-pKa) of the loading base is greater than the (log P-pKa) of the bioactive agent.

The liposomes loaded with a bioactive agent are not limited in the loading base used for loading. In some embodiments, the loading base is a weak base (e.g., the pKa of the loading base is less than 6, less than 5.5, less than 5, less than 4.5, less than 4, less than 3.5, less than 3, less than 2.5, or less than 2). In some embodiments, the loading base is a pyridine or pyridine derivative, e.g., a pyridinium, a 2-methoxy-pyridinium, a nicotinamide or a pyridazinium (e.g., a pyridinium ion, a 2-methoxy-pyridinium ion, or a pyridazinium ion; e.g., a pyridinium salt, a 2-methoxy-pyridinium salt, or a pyridazinium salt). In some embodiments, the log P of the loading base is less than 1.5, less than 1.0, less than 0.5, less than 0.0, or less than −0.5.

Furthermore, the technology is not limited in the bioactive agent loaded into the liposomes. For instance, some embodiments provide that the bioactive agent is an analgesic, e.g., an opioid. In some embodiments, the bioactive agent is hydromorphone, chloroquine, naltrexone, or buprenorphine. In some embodiments, the bioactive agent is an antitumor agent, an anaesthetic, an analgesic, an antimicrobial agent, a hormone, an antiasthmatic agent, a cardiac glycoside, an antihypertensive, a vaccine, an antiarrhythmic, an immunomodulator, a steroid, a monoclonal antibody, a neurotransmitter, a radionuclide, a radio contrast agent, a nucleic acid, a protein, a herbicide, a pesticide, and/or suitable combinations thereof.

Some embodiments are related to pharmaceutical compositions. Accordingly, in some embodiments the compositions provided comprise an excipient and/or a pharmaceutically acceptable carrier.

The technology provides for the efficient loading of liposomes with a bioactive agent. For example, in some embodiments the efficiency of loading is from 80 to 100%, e.g., in some embodiments the amount of bioactive agent in the intraliposomal space is greater than approximately 80%, greater than approximately 85%, greater than approximately 90%, or greater than approximately 95% of the total amount of bioactive agent in the composition.

Some embodiments provide a liposomal system comprising an aqueous medium having dispersed therein liposomes encapsulating a loading base in the intraliposomal space; and a bioactive agent, wherein the loading base has a pKa that is less than a pKa of the bioactive agent. In some embodiments of systems, the (log P-pKa) of the loading base is greater than the (log P-pKa) of the bioactive agent.

Associated embodiments of methods are provided. For example, in some embodiments the technology provides a method of preparing a composition of liposomes for loading with a bioactive agent, the method comprising preparing liposomes in a solution comprising a salt of a loading base; and removing, substantially removing, essentially removing, effectively removing, and/or decreasing the concentration of the salt of the loading base from the extraliposomal space (e.g., by sedimentation in a centrifuge, dialysis, dilution, gel chromatography, etc.) to produce a composition of liposomes for loading with a bioactive agent, wherein the loading base has a pKa lower than the pKa of the bioactive agent. Some embodiments comprise a step of adding a loading medium to the extraliposomal space, the loading medium having a pH greater than the pKa of the loading base.

The methods for preparing liposome compositions for preparing liposomes loaded with a bioactive agent are not limited in the loading base used in the provided methods. In some embodiments, the loading base is a weak base (e.g., the pKa of the loading base is less than 6, less than 5.5, less than 5, less than 4.5, less than 4, less than 3.5, less than 3, less than 2.5, or less than 2). In some embodiments, the loading base is a pyridine or pyridine derivative, e.g., a pyridinium, a 2-methoxy-pyridinium, or a pyridazinium (e.g., a pyridinium ion, a 2-methoxy-pyridinium ion, a nicotinamide or a pyridazinium ion; e.g., a pyridinium salt, a 2-methoxy-pyridinium salt, or a pyridazinium salt). In some embodiments, the log P of the loading base is less than 1.5, less than 1.0, less than 0.5, less than 0.0, or less than −0.5.

Further embodiments of methods are related to loading liposomes with a bioactive agent. For example, some embodiments provide methods for preparing liposomes encapsulating a bioactive agent, the method comprising providing a composition comprising liposomes, the liposomes comprising a loading base in an intraliposomal space; and adding a bioactive agent to the composition, wherein the loading base has a pKa that is lower than the pKa of the bioactive agent. Some embodiments comprise a step of providing a loading medium in the extraliposomal space comprising a pH that is greater than the pKa of the bioactive agent.

The methods for loading liposomes with a bioactive agent are not limited in the loading base used in the liposome loading methods. In some embodiments, the loading base is a weak base (e.g., the pKa of the loading base is less than 6, less than 5.5, less than 5, less than 4.5, less than 4, less than 3.5, less than 3, less than 2.5, or less than 2). In some embodiments, the loading base is a pyridine or pyridine derivative, e.g., a pyridinium, a 2-methoxy-pyridinium, or a pyridazinium (e.g., a pyridinium ion, a 2-methoxy-pyridinium ion, a nicotinamide or a pyridazinium ion; e.g., a pyridinium salt, a 2-methoxy-pyridinium salt, or a pyridazinium salt). In some embodiments, the log P of the loading base is less than 1.5, less than 1.0, less than 0.5, less than 0.0, or less than −0.5.

Some embodiments provide a liposome composition for preparing liposomes loaded with a bioactive agent, the composition comprising liposomes, the liposomes comprising a diprotic acid or a salt of a diprotic acid, wherein the first pKa and the second pKa of the diprotic acid are both less than zero. For example, in some embodiments the diprotic acid is a sulfonate, e.g., a disulfonate such as, e.g., methanedisulfonic acid; 1,2-ethanedisulfonic acid (edisylate); or 1,3-propanedisulfonic acid (eprodisate). Related embodiments provide a liposomal system comprising an aqueous medium having dispersed therein liposomes encapsulating a diprotic acid or a salt of a diprotic acid, wherein the first pKa and the second pKa of the diprotic acid are both less than zero; and a bioactive agent. In some embodiments, the diprotic acid is a sulfonate, e.g., a disulfonate such as, e.g., methanedisulfonic acid; 1,2-ethanedisulfonic acid (edisylate); or 1,3-propanedisulfonic acid (eprodisate). Embodiments of methods for producing a composition of liposomes for loading with a bioactive agent comprise the steps of preparing liposomes in a solution comprising a diprotic acid or a salt of a diprotic acid, wherein the first pKa and the second pKa of the diprotic acid are both less than zero; and removing the diprotic acid or a salt of a diprotic acid from the extraliposomal space to produce a composition of liposomes for loading with a bioactive agent. In some embodiments of the methods, the diprotic acid is a sulfonate (e.g., disulfonate), e.g., methanedisulfonic acid; 1,2-ethanedisulfonic acid (edisylate); or 1,3-propanedisulfonic acid (eprodisate). Related embodiments of methods for preparing liposomes comprising a bioactive agent comprise providing a composition comprising liposomes, the liposomes comprising a diprotic acid or a salt of a diprotic acid, wherein the first pKa and the second pKa of the diprotic acid are both less than zero; and adding a bioactive agent to the composition. In some embodiments, the diprotic acid is a sulfonate, e.g., a disulfonate such as, e.g., methanedisulfonic acid; 1,2-ethanedisulfonic acid (edisylate); or 1,3-propanedisulfonic acid (eprodisate).

Also provided are methods for producing liposomes by dissolving lipids in a solvent to produce a lipid solution; adding a weak base salt (e.g., a sulfate, an eprodisate, or an edisylate) to the lipid solution to produce liposomes. In some embodiments, the lipids are dry powders. In some embodiments, the solvent is an alcohol. In some embodiments, the solvent is miscible with aqueous solutions and/or the solvent has significant aqueous solubility, e.g., the alcohol is sufficiently soluble in water to form a single phase at the desired alcohol to water ratio, e.g., an alcohol that has an aqueous solubility of at least 50 g/L (e.g., 50, 55, 60, 65, 70, 75, 80, 85, 90, 95, 100, 105, 110, 115, 120, 125, 130, 135, 140, 145, or 150 g/L aqueous solubility) or, more preferably, an aqueous solubility of more than 150 g/L (e.g., more than 150, 160, 170, 180, 190, 200, 250, 300 g/L, or more g/L, or completely miscible at any ratio).

For example, in some embodiments the solvent is an alcohol such as, e.g., 2-propanol, t-butanol, methanol, ethanol, 1-prop anol, 2-butanol, isobutanol, 1-butanol, and/or 1-pentanol and isomers of 1-pentanol. However, the technology is not limited to these solvents. Any solvent that provides for the production of liposomes according to the technology provided herein.

For example, data collected during the development of embodiments of the technology indicate that efficient liposome loading is provided by methods that comprise use of an alcohol that is sufficiently nonpolar to solvate the lipids used to prepare the liposomes and partition significantly into the hydrophobic (e.g., oil) phase while also being sufficiently polar to allow the alcohol to be washed away and/or diluted once the liposomes are prepared. Accordingly, embodiments comprise use of an alcohol that has a Log P value that is between approximately −0.2 to 1.0 and preferably between approximately 0.1 to 0.8. Alternatively, the alcohol may be chosen based on the number of carbons in the alcohol. For example, in some embodiments the alcohol used to prepare liposomes has 1 to 6 carbon atoms (e.g., 1, 2, 4, 5, 6, or 6 carbon atoms). In some particular embodiments, the alcohol has 3 or 4 carbon atoms.

In some embodiments, the dissolving comprises warming the lipids and solvent to 40 to 85° C. or 40° C. to 70° C. In some embodiments, the method comprises warming the weak base salt to 40 to 85° C. or 40° C. to 70° C. prior to adding the weak base salt to the lipid solution. Related embodiments comprise an additional step of cooling the liposomes to a temperature that is below the phase transition temperature of the lipids and, in some embodiments, the methods comprise a further step of diluting the liposomes in an aqueous solution. In some embodiments the methods comprise washing the liposomes to remove weak base salt from the extraliposomal space. In some embodiments, the solvent is methanol, ethanol, 1-propanol, 2-propanol, 2-butanol, 1-butanol or t-butanol.

In particular embodiments, the weak base salt is added to the lipid solution in a plurality of volumes (e.g., two or more volumes that are added separately to the lipid solution). For example, in some embodiments adding the weak base salt to the lipid solution comprises adding a first volume of the weak base salt to the lipid solution followed by adding a second volume of the weak base salt to the lipid solution. In some embodiments, the ratio of the first volume to the second volume is 5:1 to 1:5 (e.g., 5:1, 4.5:1, 4:1, 3.5:1, 3:1, 2.5:1, 2:1, 1.5:1, 1:1, 1:1.5, 1:2, 1:2.5, 1:3, 1:3.5, 1:4, 1:4.5, or 1:5).

Embodiments of the method find use in encapsulating a bioactive agent in the intraliposomal space. Accordingly, the technology provides embodiments of methods comprising providing a composition of liposomes prepared by a method as described above; and adding a bioactive agent to the composition of liposomes.

Associated methods relate to a method of treating a subject in need of pain reduction, the method comprising administering to the subject a composition as described herein. In some embodiments, methods of treating a subject further comprise assessing the subject's pain.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings.

Figure 1:
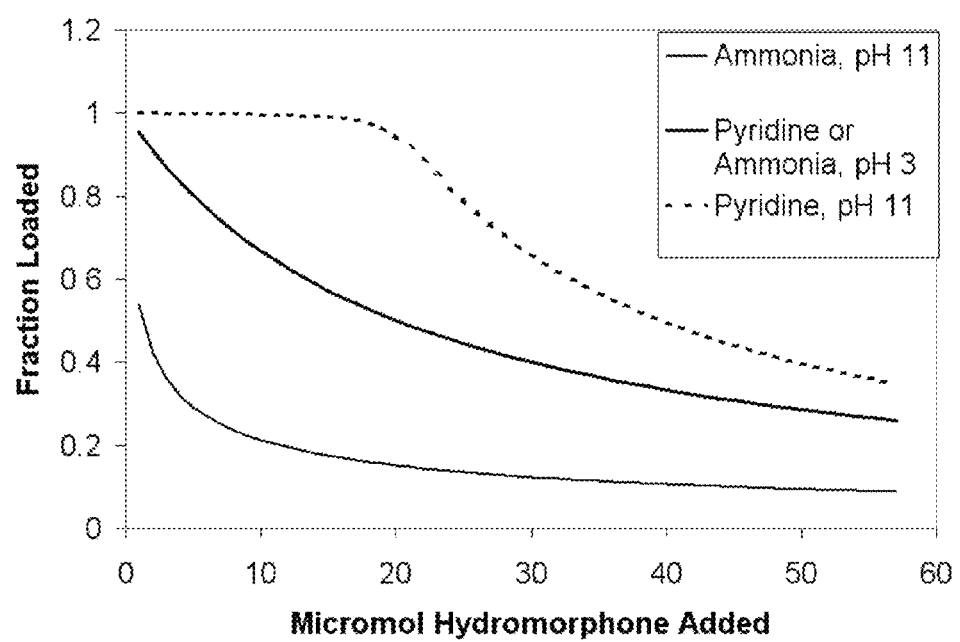
FIG. 1 is a plot showing the theoretical loading curves for loading of hydromorphone into liposomes containing 20 μmol ammonium or pyridinium.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

Provided herein is a technology related to using weak bases as the loading base to load drugs efficiently into liposomes. In particular, experiments were conducted indicating that drugs such as chloroquine, hydromorphone, naltrexone, and buprenorphine are loaded into liposomes with high efficiency using a weak base such as pyridine and related molecules (e.g., 2-methoxypridine, pyridazine, etc.) or nicotinamide. The data collected indicated that the technology provides a high loading efficiency and the in vitro leakage of the drug from the liposomes in the early phase of leakage (0-48 hrs) was very low. In some embodiments, the weak loading bases act as sacrificial leakage agents that are leaked from the liposomes rather than the drug.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein. The section headings used herein are for organizational purposes only and are not to be construed as limiting the described subject matter in any way.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the technology may be readily combined, without departing from the scope or spirit of the technology.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

The term "lipid" refers to any suitable material resulting in a bilayer such that the hydrophobic portion of the lipid material orients toward the bilayer interior while the hydrophilic portion orients toward the aqueous phase. Hydrophilic characteristics derive from the presence of phosphato, carboxylic, sulfato, amino, sulfhydryl, nitro, and other like groups. Hydrophobicity could be conferred by the inclusion of groups that include, but are not limited to, long chain saturated and unsaturated aliphatic hydrocarbon groups and such groups substituted by one or more aromatic, cycloaliphatic or heterocyclic group(s).

Amphipathic lipids often find use as the primary lipid vesicle structural element. Examples of amphipathic compounds are phosphoglycerides and sphingolipids, representative examples of which include phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoyl-phosphatidylcholine, dioleoylphosphatidylcholine, distearoylphosphatidylcholine, and dilinoleoylphosphatidylcholine. Other compounds lacking in phosphorus, such as sphingolipid and glycosphingolipid families are also within the group designated as lipid. Additionally, the amphipathic lipids described above may be mixed with other lipids including triacyglycerols and sterols.

"Phospholipid" refers to any one phospholipid or combination of phospholipids capable of forming liposomes.

Phosphatidylcholines (PC), including those obtained from egg, soy beans, or other plant sources or those that are partially or wholly synthetic, or of variable lipid chain length and unsaturation find use in embodiments of the present technology. Synthetic, semisynthetic, and natural product phosphatidylcholines including, but not limited to, distearoylphosphatidylcholine (DSPC), hydrogenated soy phosphatidylcholine (HSPC), soy phosphatidylcholine (soy PC), egg phosphatidylcholine (egg PC), hydrogenated egg phosphatidylcholine (HEPC), dip almitoylphosphatidylcholine (DPPC), and dimyristoylphosphatidylcholine (DMPC) are suitable phosphatidylcholines for use in this technology. All of these phospholipids are commercially available.

Further, phosphatidylglycerols (PG) and phosphatic acid (PA) are also suitable phospholipids for use in the present technology and include, but are not limited to, dimyristoylphosphatidylglycerol (DMPG), dilaurylphosphatidylglycerol (DLPG), dip almitoylphosphatidylglycerol (DPPG), distearoylphosphatidylglycerol (DSPG) dimyristoylphosphatidic acid (DMPA), distearoylphosphatidic acid (DSPA), dilaurylphosphatidic acid (DLPA), and dipalmitoylphosphatidic acid (DPPA). Other suitable phospholipids include phosphatidylethanolamines, phosphatidylinositols, and phosphatidic acids containing lauric, myristic, stearoyl, and palmitic acid chains. Further, incorporation of polyethylene glycol (PEG) containing phospholipids is also contemplated by the present technology. It is contemplated by this technology to include cholesterol optionally in the liposomal formulation. Cholesterol is known to improve liposome stability and prevent loss of phospholipid to lipoproteins in vivo.

"Unilamellar liposomes", also referred to as "single lamellar vesicles," are spherical vesicles that include one lipid bilayer membrane that defines a single closed aqueous compartment. The bilayer membrane includes two layers (or "leaflets") of lipids; an inner layer and an outer layer. The outer layer of the lipid molecules is oriented with the hydrophilic head portions toward the external aqueous environment and the hydrophobic tails pointed downward toward the interior of the liposome. The inner layer of the lipid lay directly beneath the outer layer with the lipids oriented with the heads facing the aqueous interior of the liposome and the tails oriented toward the tails of the outer layer of lipid.

"Multilamellar liposomes" also referred to as "multilamellar vesicles" or "multiple lamellar vesicles," include more than one lipid bilayer membrane, which membranes define more than one closed aqueous compartment. The membranes are concentrically arranged so that the different membranes are separated by aqueous compartments, much like an onion.

The terms "bioactive agent" and "pharmaceutical agent" (e.g., a "drug") are used interchangeably and include but are not limited to, an antibiotic, an analgesic, an anesthetic, an antiacne agent, an antibiotic, an antibacterial, an anticancer agent, an anticholinergic, an anticoagulant, an antidyskinetic, an antiemetic, an antifibrotic, an antifungal, an antiglaucoma agent, an anti-inflammatory, an antineoplastic, an antiosteoporotic, an antipagetic, an anti-Parkinson's agent, an antisporatic, an antipyretic, an antiseptic, an antithrombotic, an antiviral, an antimalarial, an antiparasitic, a calcium regulator, a keratolytic, and/or a sclerosing agent.

The terms "encapsulation" and "entrapped," as used herein, refer to the incorporation or association of a biologically active (e.g., a pharmaceutical agent) in or with a liposome. The pharmaceutical agent may be associated with the lipid bilayer or present in the aqueous interior ("intraliposomal space") of the liposome, or both. In one embodiment, a portion of the encapsulated pharmaceutical agent takes the form of a precipitated salt in the interior of the liposome. The pharmaceutical agent may also self-precipitate in the interior of the liposome.

As used herein, a "liposome loading agent" refers to a substance (e.g., chemical, molecule, etc.) that promotes the movement of another substance (e.g., a drug) into the intraliposomal space (e.g., the lumen) of a liposome. The liposome loading agent may preferably be a counterion or counterion excipient that can initiate or facilitate drug loading and may also initiate or facilitate precipitation of the pharmaceutical agent in the aqueous interior of the liposome. Examples of liposome loading agents include, but are not limited to, weak bases and salts thereof as well as the acid, sodium or ammonium forms of monovalent anions such as chloride, acetate, lactobionate and formate; divalent anions such as aspartate, succinate and sulfate; and trivalent ions such as citrate and phosphate.

As used herein, the term "log P" refers to the logarithm of the partition coefficient (P) describing the ratio of concentrations of a compound in a mixture of two immiscible phases at equilibrium. In particular, the log P as used herein refers to the distribution between two reference phases, e.g., water and a non-aqueous-miscible liquid, e.g., an organic solvent, e.g., n-octanol. In some embodiments, log P values are theoretically calculated, e.g., using a group additivity approach or, in some embodiments, a method including factors such as dipole moment, molecular size, molecular shape, etc. See, e.g., Viswanadhan, et al (1989, *J. Chem. Inf. Comput. Sci* 29(3): 163; Suzuki and Kudo (1990), *J. Comput. Aided Mol. Des.* 4(2): 155-98, each incorporated herein by reference. Thus, the partition coefficient is a measure of how hydrophilic or hydrophobic a chemical substance is. Accordingly, partition coefficients are useful in estimating the distribution of drugs within the body.

As used herein, the "loading efficiency" refers to the amount of a substance that is incorporated into a liposome (e.g., in the intraliposomal space) by a liposome loading process relative to the total amount of the substance added. Generally, a liposome preparation is prepared for loading with a substance such as a drug; then, a known initial amount of the substance (e.g., drug) is added to the preparation. The substance (e.g., drug) is initially in the extraliposomal space and some amount of the substance (e.g., drug) moves into and becomes entrapped in the intraliposomal space. The ratio (e.g., expressed as a percentage, fraction, ratio, etc.) of entrapped substance (e.g., drug) relative to the known initial amount of the substance (e.g., drug) is a measure of the loading efficiency.

As used herein, "treat" or "treating" refers to: (i) preventing a pathologic condition (e.g., breast cancer; sepsis) from occurring (e.g. prophylaxis) or preventing symptoms related to the same; (ii) inhibiting the pathologic condition or arresting its development or inhibiting or arresting symptoms related to the same; or (iii) relieving the pathologic condition or relieving symptoms related to the same.

As used herein, the terms "subject" and "patient" refer to any animal, such as a mammal like a dog, cat, bird, livestock, and preferably a human.

As used herein, the term "effective amount" refers to the amount of a composition sufficient to effect beneficial or desired results. An effective amount can be administered in one or more administrations, applications, or dosages and is not intended to be limited to a particular formulation or administration route.

As used herein, the term "administration" refers to the act of giving a drug, prodrug, or other agent, or therapeutic treatment to a subject. Exemplary routes of administration to the human body can be through the eyes (ophthalmic), mouth (oral), skin (transdermal, topical), nose (nasal), lungs (inhalant), oral mucosa (buccal), ear, by injection (e.g., intravenously, subcutaneously, intratumorally, intraperitoneally, etc.), and the like.

As used herein, the term "pharmaceutical composition" refers to the combination of a biological agent with a carrier, inert or active, making the composition especially suitable for therapeutic use.

The terms "pharmaceutically acceptable" or "pharmacologically acceptable", as used herein, refer to compositions that do not substantially produce adverse reactions, e.g., toxic, allergic, or immunological reactions, when administered to a subject.

As used herein, the term "treating" includes reducing or alleviating at least one adverse effect or symptom of a disease or disorder through introducing in any way a therapeutic composition of the present technology into or onto the body of a subject. "Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

As used herein, "therapeutically effective dose" refers to an amount of a therapeutic agent sufficient to bring about a beneficial or desired clinical effect. The dose can be administered in one or more administrations. However, the precise determination of what would be considered an effective dose may be based on factors individual to each patient, including, but not limited to, the patient's age, size, type or extent of disease, stage of the disease, route of administration, the type or extent of supplemental therapy used, ongoing disease process, and type of treatment desired (e.g., aggressive versus conventional treatment).

Description

The technology provided herein relates to the use of weak bases as a loading base to load drugs efficiently into liposomes. Exemplary weak bases include but are not limited to pyridine, 2-methoxypyridine, pyridazine, and nicotinamide.

Liposomes

Liposomes, or lipid vesicles, are used for drug delivery to improve the therapeutic activity and increase the safety of a number of different pharmaceutical agents. Liposomal carrier systems (e.g., vesicles) are microscopic spheres of one or more lipid bilayers arranged around an aqueous core. The vesicles have been shown to be suitable as carriers for both hydrophilic and hydrophobic therapeutic agents owing to their unique combination of lipophilic and hydrophilic portions.

Liposomes are completely closed lipid bilayer membranes containing an entrapped volume. The bilayer membrane separates this surrounded volume (the "intraliposomal space" or "lumen") from the bulk phase (the "extraliposomal space"). Liposomes may be unilamellar vesicles (possessing a single membrane bilayer) or multilamellar vesicles (onion-like structures characterized by multiple membrane bilayers, each separated from the next by an aqueous layer). Liposomes may take other forms as well, e.g., multivesicular liposomes (MVL), which are lipid vesicles with multiple internal aqueous chambers formed by non-concentric layers and having internal membranes distributed as a network throughout the MVL.

In these various forms, the bilayer is composed of two lipid monolayers having a hydrophobic "tail" region and a hydrophilic "head" region. The structure of the membrane bilayer is such that the hydrophobic (nonpolar) "tails" of the lipid monolayers orient toward the center of the bilayer while the hydrophilic "heads" orient towards the aqueous phase.

Liposome Formation

In a conventional liposome preparation such as that of Bangham et al. (J. Mol. Biol., 1965, 13: 238-252), phospholipids were suspended in an organic solvent that was then evaporated to dryness to leave a phospholipid film on the reaction vessel. Next, an appropriate amount of aqueous phase was added, the mixture was allowed to "swell", and the resulting MLVs were dispersed by mechanical means to produce multilamellar vesicles. This preparation provided the basis for the development of the small sonicated unilamellar vesicles described by Papahadjopoulos et al. (Biochim. Biophys, Acta., 1967, 135: 624-638) and multilamellar vesicles.

Subsequently, techniques for producing large unilamellar vesicles (LUVs) such as reverse phase evaporation, infusion procedures, and detergent dilution were used to produce liposomes. A review of these and other methods for producing liposomes may be found in the text Liposomes, Marc Ostro, ed., Marcel Dekker, Inc., New York, 1983, Chapter 1. See also Szoka Jr. et al., (1980, Ann. Rev. Biophys. Bioeng., 9:467). One particular method for forming LUVs is described in Cullis et al., PCT Publication No. 87/00238, Jan. 16, 1986, entitled "Extrusion Technique for Producing Unilamellar Vesicles".

In some embodiments, liposomes that are used in the present technology are formed from standard vesicle-forming lipids, which generally include neutral and negatively charged phospholipids and a sterol, such as cholesterol. The selection of lipids is generally guided by consideration of, e.g., liposome size and stability of the liposomes in the bloodstream.

Various types of lipids are used to produce liposomes. For example, amphipathic lipids that find use are zwitterionic, acidic, or cationic lipids. Examples of zwitterionic amphipathic lipids are phosphatidylcholines, phosphatidyl-ethanolamines, sphingomyelins, etc. Examples of acidic amphipathic lipids are phosphatidylglycerols, phosphatidylserines, phosphatidylinositols, phosphatidic acids, etc. Examples of cationic amphipathic lipids are diacyl trimethylammonium propanes, diacyl dimethylammonium propanes, stearylamine, etc. Examples of neutral lipids include diglycerides, such as diolein, dipalmitolein, and mixed caprylin-caprin; triglycerides, such as triolein, tripalmitolein, trilinolein, tricaprylin, and trilaurin; and combinations thereof. Additionally, cholesterol or plant sterols are used in some embodiments, e.g., to make multivesicular liposomes.

In some embodiments, the major lipid component in the liposomes is phosphatidylcholine. Phosphatidylcholines having a variety of acyl chain groups of varying chain length and degree of saturation are available or may be isolated or synthesized by well-known techniques. In general, less saturated phosphatidylcholines are more easily sized, particularly when the liposomes must be sized below approximately 0.3 microns, e.g., for purposes of filter sterilization. In some embodiments, phosphatidylcholines containing saturated fatty acids with carbon chain lengths in the range of approximately $C_{14}$ to $C_{22}$ are preferred. Phosphatidylcholines with monounsaturated or diunsaturated fatty acids and mixtures of saturated and unsaturated fatty acids are used in some embodiments. Other suitable lipids include phosphonolipids in which the fatty acids are linked to glycerol via ether linkages rather than ester linkages (e.g., as found in some members of the Archaea). Liposomes useful in the present technology may also be composed of sphingomyelin or phospholipids with head groups other than choline, such as ethanolamine, serine, glycerol, and inositol. In some embodiments, liposomes include a sterol, preferably cholesterol, at molar ratios of from 0.1 to 1.0 of the cholesterol to the phospholipid). In some embodiments, the liposome compositions are distearoylphosphatidylcholine/cholesterol, dipalmitoylphosphatidylcholine/cholesterol, or sphingomyelin/cholesterol. Methods used in sizing and filter-sterilizing liposomes are provided below.

A variety of methods are available for preparing liposomes as described in, e.g., Szoka et al., Ann. Rev. Biophys. Bioeng. 9:467 (1980), U.S. Pat. Nos. 4,235,871; 4,501,728; and 4,837,028; the text Liposomes, Marc J. Ostro, ed., Marcel Dekker, Inc., New York, 1983, Chapter 1, and Hope, et al., Chem. Phys. Lip. 40:89 (1986), each of which is incorporated herein by reference. One exemplary method produces multilamellar vesicles of heterogeneous sizes. In this method, the vesicle-forming lipids are dissolved in a suitable organic solvent or solvent system and dried under vacuum or an inert gas to form a thin lipid film. Alternatively, the lipids may be dissolved in a suitable solvent, such as tertiary butanol, and then lyophilized to form a more homogeneous lipid mixture that is in a more easily hydrated, microporous, powder-like form. This film or powder is covered with an aqueous solution (e.g., in some embodiments, an aqueous buffered solution) and allowed to hydrate, typically over a 15-60 minute period with agitation. The size distribution of the resulting multilamellar vesicles can be shifted toward smaller sizes by hydrating the lipids under more vigorous agitation conditions or by adding solubilizing detergents such as deoxycholate.

Many different types of organic solvents such as ethers, hydrocarbons, halogenated hydrocarbons, and/or freons are used in some embodiments as the solvent in the lipid component. For example, diethyl ether, isopropyl ether, and other ethers; chloroform; tetrahydrofuran; halogenated ethers; esters, and combinations thereof find use in the present technology.

Several techniques are available for sizing liposomes to a desired size. One sizing method is described in U.S. Pat. No. 4,737,323, incorporated herein by reference. Sonicating a liposome suspension either by bath or probe sonication produces a progressive size reduction down to small unilamellar vesicles less than approximately 0.05 microns in size. Homogenization is another method that relies on shearing energy to fragment large liposomes into smaller ones. In a typical homogenization procedure, multilamellar vesicles are recirculated through a standard emulsion homogenizer until selected liposome sizes, typically between approximately 0.1 and 0.5 microns, are observed. In both methods, the particle size distribution can be monitored by conventional laser-beam particle size discrimination.

In some embodiments, extrusion of liposomes through a small-pore polycarbonate membrane or an asymmetric ceramic membrane provides an effective method for reducing liposome sizes to a relatively well-defined size distribution. Typically, the suspension is cycled through the membrane one or more times until the desired liposome size distribution is achieved. The liposomes may be extruded through successively smaller-pore membranes to achieve a gradual reduction in liposome size. In some embodiments comprising use of extrusion methods, liposomes find use that have a size of from approximately 0.05 microns to approximately 0.15 microns. In some embodiments, liposomes are not extruded. For example, in some embodiments the liposomes are approximately 1 micron to 10 microns in diameter. While many technologies and sizes for liposomes are discussed herein, the technology is not dependent on the size of the liposomes; accordingly, there is no size preference for the liposome loading technology per se.

In some embodiments, liposomes are prepared, for example, by weighing out a quantity of a phosphatidylcholine (optionally cholesterol and/or optionally a phosphatidylglycerol) and dissolving them in an organic solvent, e.g., chloroform and methanol in a 1:1 mixture (v/v) or alternatively in neat chloroform. The solution is evaporated to form a solid lipid phase such as a film or a powder, for example, with a rotary evaporator, spray dryer, or other method. The film or powder is then hydrated with an aqueous solution optionally containing an excipient and having a pH range from approximately 2.0 to approximately 7.4 to form a liposome dispersion. The lipid film or powder dispersed in the aqueous solution is heated to a temperature from approximately 25° C. to approximately 70° C. depending on the phospholipids used.

Multilamellar liposomes are formed, e.g., by agitation of the dispersion, preferably through the use of a thin-film evaporator apparatus such as is described in U.S. Pat. No. 4,935,171 or through shaking or vortex mixing. Unilamellar vesicles are formed by the application of a shearing force to an aqueous dispersion of the lipid solid phase, e.g., by sonication or the use of a microfluidizing apparatus such as a homogenizer or a French press. Shearing force can also be applied using injection, freezing and thawing, dialyzing away a detergent solution from lipids, or other known methods used to prepare liposomes. The size of the liposomes can be controlled using a variety of known techniques including controlling the duration of shearing force. In some embodiments, a homogenizing apparatus is employed to produce unilamellar vesicles having diameters of less than 200 nanometers at a pressure of 3,000 to 14,000 psi (e.g., 10,000 to 14,000 psi) and a temperature that is approximately at the aggregate transition temperature of the lipids. In some exemplary embodiments, liposomes are prepared as described below in the Methods section of the included Examples.

According to some embodiments, liposomes are produced by combining lipids in chloroform, removing solvent to create a component mixture, suspending the lipid in a suitable liquid (e.g., an alcohol such as, e.g., t-butanol), and lyophilizing the suspension. Then, according to some embodiments for loading liposomes with a bioactive agent, the microporous lipid mass is subsequently hydrated using a weak base salt. In addition, provided herein are embodiments of the technology that eliminate the first steps (e.g., dissolving lipids in chloroform and removing the solvent) commonly used for the preparation of liposomes. For example, some embodiments comprise a step of dissolving lipids in a suitable liquid (e.g., an alcohol such as, e.g., t-butanol) directly without a preceding step of mixing the lipid components in chloroform. In some embodiments, dissolving lipids in a suitable liquid (e.g., an alcohol such as, e.g., t-butanol) is associated with heating the liquid to facilitate dissolving the lipid in the liquid. In some embodiments, the heating comprises providing an amount of heat to the liquid (e.g., a liquid comprising the lipid) that raises the temperature of the liquid sufficiently to dissolve the lipids therein (e.g. raising the temperature by 1 to 60 degrees (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 degrees Celsius)).

Additional embodiments of liposome preparation methods provided herein eliminate the lyophilizing step. For example, some embodiments prepare liposomes directly from lipids provided as dry powders. In particular, some embodiments of the methods described herein comprise providing lipids (e.g., phospholipid, cholesterol, etc.) as powders, dissolving the lipids in a suitable liquid (e.g., an alcohol such as, e.g., 1- or 2-propanol), and adding a base salt to the lipid solution to produce liposomes. In some embodiments, dissolving lipids in a suitable liquid (e.g., an alcohol such as, e.g., 1- or 2-propanol) is associated with heating the liquid to facilitate dissolving the lipid in the liquid. In some embodiments, the heating comprises providing an amount of heat to the liquid (e.g., a liquid comprising the lipid) that raises the temperature of the liquid sufficiently to dissolve the lipids therein (e.g. raising the temperature by 1 to 20 degrees (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 degrees Celsius). During the development of embodiments of the technology provided herein, experiments were conducted to evaluate producing liposomes directly from lipids (e.g., powdered lipids). See, e.g., Examples 10-14. For example, data collected from these experiments indicated that producing liposomes directly from lipids (e.g., powdered lipids) is efficient—the methods incorporated approximately 25% of the base salt into the liposomes and the methods form liposomes that are comparable in their properties to those formed by present methods comprising hydrating lyophilized lipid mixtures. Further, the liposomes can be readily washed by sedimentation at low g forces. In some embodiments, the liposomes are formed from dipalmitoyl phosphatidylcholine (DPPC), distearoyl phosphatidylcholine (DSPC), and/or a hydrogenated soybean phospholipid comprising a mixture of stearoyl and palmitoyl phosphatidyl choline.

Accordingly, in some embodiments, the present invention provides of producing liposomes, the method comprising: a) dissolving lipids in a solvent to produce a lipid solution; b) adding an aqueous solution to the lipid solution to produce liposomes. In some embodiments, the solvent is miscible with aqueous solutions or is a solvent that has significant aqueous solubility. In some embodiments, the solvent is an alcohol. In some embodiments, the solvent is selected from the group consisting of methanol, ethanol, 1-propanol, 2-propanol, 2-butanol, 1-butanol and t-butanol. In some embodiments, the solvent is selected from the group consisting of a C3 and a C4 alcohol. In some embodiments, the C3 alcohol is 1-propanol. In some embodiments, the C4 alcohol is 2-butanol.

In some embodiments, the lipids comprise phospholipids. In some embodiments, the phospholipids and the solvent are combined at a concentration of about 400 mg to 800 mg phospholipids per 1 ml of solvent. In some embodiments, the phospholipids and the solvent are combined at a concentration of about 500 mg to 700 mg phospholipids per 1 ml of solvent. In some embodiments, the phospholipids and the solvent are combined at a concentration of about 550 mg to 650 mg phospholipids per 1 ml of solvent.

In some embodiments, the lipids further comprise cholesterol. In some embodiments, the cholesterol and the solvent are combined at a concentration of about 50 mg to 250 mg cholesterol per 1 ml of solvent. In some embodiments, the cholesterol and the solvent are combined at a concentration of about 100 mg to 200 mg cholesterol per 1 ml of solvent. In some embodiments, the cholesterol and the solvent are combined at a concentration of about 125 mg to 175 mg cholesterol per 1 ml of solvent.

In some embodiments, the dissolving step comprises warming the lipids and solvent to 40 to 85° C. or 40 to 70° C. In some embodiments, the methods further comprise warming the aqueous solution to 40 to 85° C. or 40 to 70° C. prior to addition to the lipid solution. In some embodiments, the lipids and solvent are dissolved in a vessel to provide a dissolved lipid composition and the aqueous solution is injected into the vessel containing the dissolved lipid composition. In some embodiments, the methods further comprise cooling the liposomes to a temperature that is below the phase transition temperature of the lipids.

In some embodiments, the aqueous solution comprises a liposome loading agent as described elsewhere herein. In some embodiments, the aqueous solution is selected from the group consisting of an acidic solution and a basic solution. In some embodiments, the aqueous solution comprises liposome loading agent selected from the group consisting of counter ions and salts thereof. In some embodiments, the aqueous solution comprises a weak base salt selected from the group consisting of a sulfate, an eprodisate, and an edisylate. In some embodiments, adding the weak base salt to the lipid solution comprises adding a first volume of the weak base salt to the lipid solution followed by adding a second volume of the weak base salt to the lipid solution. In some embodiments, the ratio of the first volume to the second volume is 5:1 to 1:5.

In some embodiments, the aqueous solution comprises an encapsulant, e.g., a compound or molecule that is designated to be encapsulated into the intraliposomal space. Examples of encapsulants, and particularly bioactive agents, are described in detail herein. In some embodiments, the encapsulant is selected from the group consisting of a chemical bioactive agent and a biologic bioactive agent. In some embodiments, the chemical bioactive agent is an analgesic.

In some embodiments, the methods further comprise diluting the liposomes in an aqueous solution. In some embodiments, the methods further comprise washing the liposomes to remove liposome loading agents or encapsulants, if utilized, from the extraliposomal space.

In some embodiments, the present invention provides methods for preparing liposomes encapsulating a bioactive agent, the method comprising providing a composition of liposomes prepared with a liposome loading agent as described above and adding a bioactive agent to the composition of liposomes under conditions such that the bioactive agent is transported to the intraliposomal space of the liposomes.

In some embodiments, the present invention provides a liposome composition made by the methods described above. In some embodiments, the liposome compositions are used for treatment of disease or condition in an animal.

Bioactive Agents

In some embodiments, biological substances and/or therapeutic agents (e.g., "drugs") are incorporated by encapsulation within liposomes (e.g., in the intraliposomal space). Examples of bioactive agents include but are not limited to antianginas, antiarrhythmics, antiasthmatic agents, antibiotics, antimalarials, antidiabetics, antifungals, antihistamines, antihypertensives, antiparasitics, antineoplastics, antivirals, cardiac glycosides, herbicides, hormones, immunomodulators, antibodies (e.g., monoclonal, human, humanized, chimeric, etc., antibodies), neurotransmitters, nucleic acids, pesticides, proteins, radio contrast agents, radionuclides, sedatives, analgesics, steroids, tranquilizers, vaccines, vasopressors, anesthetics, and/or peptides.

The drugs that can be incorporated into the dispersion system as therapeutic agents include chemicals as well as biologics. The term "chemicals" encompasses compounds that are classically referred to as drugs, such as antitumor agents, anesthetics, analgesics, antimicrobial agents, opiates, hormones, etc.

Of particular interest for inclusion in the liposome compositions of the present technology are analgesics, e.g., opiates and/or opioids (e.g., hydromorphone and buprenorphine), opioid antagonists (e.g., naltrexone), and quinoline drugs (e.g., a 4-aminoquinoline such as chloroquine).

The term "biologics" encompasses nucleic acids (e.g., DNA and RNA), proteins and peptides, and includes compounds such as cytokines, hormones (e.g., pituitary and hypophyseal hormones), growth factors, vaccines, etc.

Suitable antibiotics for inclusion in the liposome compositions of the present technology include, but are not limited to, loracarbef, cephalexin, cefadroxil, cefixime, ceftibuten, cefprozil, cefpodoxime, cephradine, cefuroxime, cefaclor, neomycin/polymyxin/bacitracin, dicloxacillin, nitrofurantoin, nitrofurantoin macrocrystal, nitrofurantoin/nitrofuran mac, dirithromycin, gemifloxacin, ampicillin, gatifloxacin, penicillin V potassium, ciprofloxacin, enoxacin, amoxicillin, amoxicillin/clavulanate potassium, clarithromycin, levofloxacin, moxifloxacin, azithromycin, sparfloxacin, cefdinir, ofloxacin, trovafloxacin, lomefloxacin, methenamine, erythromycin, norfloxacin, clindamycin/benzoyl peroxide, quinupristin/dalfopristin, doxycycline, amikacin sulfate, vancomycin, kanamycin, netilmicin, streptomycin, tobramycin sulfate, gentamicin sulfate, tetracyclines, framycetin, minocycline, nalidixic acid, demeclocycline, trimethoprim, miconazole, colistimethate, piperacillin sodium/tazobactam sodium, paromomycin, colistin/neomycin/hydrocortisone, amebicides, sulfisoxazole, pentamidine, sulfadiazine, clindamycin phosphate, metronidazole, oxacillin sodium, nafcillin sodium, vancomycin hydrochloride, clindamycin, cefotaxime sodium, co-trimoxazole, ticarcillin disodium, piperacillin sodium, ticarcillin disodium/clavulanate potassium, neomycin, daptomycin, cefazolin sodium, cefoxitin sodium, ceftizoxime sodium, penicillin G potassium and sodium, ceftriaxone sodium, ceftazidime, imipenem/cilastatin sodium, aztreonam, cinoxacin, erythromycin/sulfisoxazole, cefotetan disodium, ampicillin sodium/sulbactam sodium, cefoperazone sodium, cefamandole nafate, gentamicin, sulfisoxazole/phenazopyridine, tobramycin, lincomycin, neomycin/polymyxin B/gramicidin, clindamycin hydrochloride, lansoprazole/clarithromycin/amoxicillin, alatrofloxacin, linezolid, bismuth subsalicylate/metronidazole/tetracycline, erythromycin/benzoyl peroxide, mupirocin, fosfomycin, pentamidine isethionate, imipenem/cilastatin, troleandomycin, gatifloxacin, chloramphenicol, cycloserine, neomycin/polymyxin B/hydrocortisone, ertapenem, meropenem, cephalosporins, fluconazole, cefepime, sulfamethoxazole, sulfamethoxazole/trimethoprim, neomycin/polymyxin B, penicillins, rifampin/isoniazid, erythromycin estolate, erythromycin ethylsuccinate, erythromycin stearate, ampicillin trihydrate, ampicillin/probenecid, sulfasalazine, sulfanilamide, sodium sulfacetamide, dapsone, doxycycline hyclate, trimenthoprim/sulfa, methenamine mandelate, plasmodicides, pyrimethamine, hydroxychloroquine, chloroquine phosphate, chloroquine diphosphate, trichomonocides, anthelmintics, atovaquone.

Liposome Loading

Liposomes find use in pharmaceutical preparations, e.g., to improve the characteristics (e.g., bioavailability, pharmacokinetics, toxicity, etc.) of a drug or other bioactive agent ("pharmaceutical agent") when administered to a patient. In particular, therapies employing bioactive agents can in many cases be improved by encapsulating the agent in liposomes rather than administering the free agent directly into the body. For example, incorporation of such agents in liposomes can change their activities, clearance rates, tissue distributions, and toxicities compared to direct administration. Liposomes themselves have been reported to have no significant toxicities in previous human clinical trials where they have been given intravenously. See, e.g., Richardson et al., (1979), Br. J. Cancer 40:35; Ryman et al., (1983) in "Targeting of Drugs" G. Gregoriadis, et al., eds. pp 235-248, Plenum, N.Y.; Gregoriadis G., (1981), Lancet 2:241, and Lopez-Berestein et al., (1985) J. Infect. Dis., 151:704. Liposomes are reported to concentrate predominantly in the reticuloendothelial organs lined by sinusoidal capillaries, e.g., liver, spleen, and bone marrow, and phagocytosed by the phagocytic cells present in these organs.

When liposomes are used in a liposome drug delivery system, a bioactive agent such as a drug is entrapped in the liposome and then administered to the patient to be treated. For example, see Rahman et al., U.S. Pat. No. 3,993,754; Sears, U.S. Pat. No. 4,145,410; Paphadjopoulos et al., U.S. Pat. No. 4,235,871; Schneider, U.S. Pat. No. 4,224,179; Lenk et al., U.S. Pat. No. 4,522,803; and Fountain et al., U.S. Pat. No. 4,588,578. Alternatively, if the bioactive agent is lipophilic, it may associate with the lipid bilayer. Typically, the term "entrapment" includes both the drug in the aqueous volume of the liposome as well as drug associated with the lipid bilayer.

Liposome formulations for pharmaceutical applications can be made either by combining drug and lipid before formation of the vesicles or by "loading" lipid vesicles with drug after the liposomes have been formed. Upon administration to a patient, liposomes biodistribute and interact with cells in the body according to route of administration, vesicular composition, and vesicular size. Charge, chemistry, and bilayer components (e.g., the inclusion on the vesicle surface of protective polymers or targeting moieties) all change the way liposomes behave in the patient.

In some embodiments, the pharmaceutical agent is loaded into pre-formed liposomes using a loading procedure, for example, by using a pH gradient. In some embodiments, the pharmaceutical agent may precipitate in the interior of the liposome. This precipitation protects the pharmaceutical agent and the lipids from degradation (e.g., hydrolysis). In some embodiments, an excipient such as citrate or sulfate precipitates the pharmaceutical agent and can be utilized in the interior of the liposomes together with a gradient to promote drug loading.

In some embodiments, liposomal entrapment of bioactive agents is effected by employing transmembrane ion gradients (see, e.g., Int'l Pat. Appl. PCT/US1985/001501). Aside from inducing uptake, such transmembrane gradients also act to increase drug retention in the liposomes. For example, transmembrane pH gradients ($\Delta pH$) influence the drug loading of certain weak acids and weak bases. See, for example, Jacobs, Quant. Biol. 8:30-39 (1940), Chapper, et al. in Regulation of Metabolic Processes in Mitochondria, Tager, et al. eds. Elsevier, Amsterdam, pp. 293-316 (1966), Crofts, J. Biol. Chem. 242:3352-3359 (1967), Crofts, Regulatory Functions of Biological Membranes, Jarnefelt, ed., Elsevier Publishing Co., Amsterdam, pp. 247-263 (1968), Rottenberg, Bioenergetics 7:61-74 (1975), and Rottenberg, Methods in Enzmol. 55:547-569 (1979). This behavior stems from the permeable nature of the neutral forms of these molecules, which contrasts with the impermeable nature of the charged forms. Thus, if a neutral amine (such as ammonia) diffuses across a biological membrane or vesicle exhibiting a ΔpH (e.g., with an acidic interior), it will become protonated and therefore become trapped in the vesicle interior.

In some particular embodiments, ammonium sulfate is used as a liposome loading agent (e.g., a liposome loading base) under conditions where both the ammonium and the drug are predominantly in the charged (e.g., protonated) form. For example, the loading of a drug (e.g., hydromorphone) into ammonium sulfate-loaded liposomes is a function of the amount (μmol) of drug (e.g., hydromorphone) added (FIG. 1, solid lines). In particular, the loading efficiency of drug (e.g., hydromorphone) is approximately 50% for liposomes having an extraliposomal pH of approximately of 3 to 6 and an amount of added drug (e.g., hydromorphone) that is equal to the amount of ammonium in the liposomes (FIG. 1, middle solid line). However, raising the pH of the extraliposomal space to a value (e.g., 11) at which the drug (e.g., hydromorphone) (having a pKa of approximately 7.8 to 8.9) and the ammonia (having a pKa of approximately 9.3) are in the neutral form greatly diminishes the loading efficiency of drug (e.g., hydromorphone) as a function of the amount of drug (e.g., hydromorphone) added (FIG. 1, bottom solid line). This occurs because the drug (e.g., hydromorphone) is a weaker base than ammonia.

Weak Bases

Based on these observations, this phenomenon is used advantageously to load liposomes by replacing the ammonia with a substance that is a weaker base than the drug, e.g., a weak base such as pyridine or nicotinamide. Similar to the loading of ammonium sulfate-loaded liposomes, loading of a drug (e.g., hydromorphone) into liposomes loaded with a weak base salt, e.g., the sulfate salt of pyridine (having a pKa of approximately 5.3), is a function of the amount of drug (e.g., hydromorphone) added. And, when the pH of the extraliposomal compartment is 3, the loading is the same or substantially the same as the loading observed with ammonium sulfate-loaded liposomes because both the drug (e.g., hydromorphone) and the weak base (e.g., pyridine or nicotinamide) are predominantly in the charged form, even in the extraliposomal compartment (FIG. 1, middle solid line). However, as the pH of the extraliposomal compartment is raised (e.g., to 11), drug (e.g., hydromorphone) loading is elevated to near quantitative levels (e.g., nearly all drug (e.g., hydromorphone) is loaded) provided that the amount of drug (e.g., hydromorphone) added is less than the amount of weak base (e.g., pyridinium) ions inside the liposomes (see, e.g., FIG. 1, upper dashed line).

In addition to improving drug loading, using a weaker base for loading also reduces the initial rapid release rate of the drug that is observed when ammonium sulfate is used for loading. Early phase leakage is a transient, self-limiting process because leakage of a base in the neutral form lowers the internal pH of the liposomes, which in turn reduces the concentration of neutral bases. Ammonia has a log P estimated to be approximately −0.3 and a pKa of 9.3. Therefore, in this exemplary composition for loading a drug (e.g., hydromorphone) whose log P is 1.3 and pKa is approximately 7.8 to 8.9, the drug is released from the liposomes more than the residual ammonia. In contrast, a loading base that is a weaker base than the drug to be loaded (e.g., in particular, a weak base having a (log P-pKa) that is higher than the (log P-pKa) of the drug) leaks more from the liposomes than the drug. Accordingly, using a base for drug loading that is a weaker base than the drug and/or has a (log P-pKa) greater than the (log P-pKa) of the drug eliminates or minimizes the early rapid release of drug from the liposomes.

The technology is not limited in the weak base used for loading liposomes. Exemplary weak bases include pyridine, 2-methoxypyridine, pyridazine, adenine, aniline, and nicotinamide and derivatives thereof. Furthermore, the technology is not limited in the phase of the weak base used for loading liposomes. For example, both adenine (solid at room temperature) and aniline (liquid at room temperature) find use in embodiments of the technology.

Pyridine is a heterocyclic organic base having a pKa of 5.3. Pyridine is a liquid that is miscible with water at all ratios. Pyridine is hydrophobic in the neutral form, with an estimated log P of approximately 1.3. When added to a strong acid solution, pyridine is protonated to form a pyridinium salt; the pH varies over the range of 3 to 7 depending on the proportion of pyridine to acid used.

2-methoxypyridine is a pyridine derivative having a pKa of 3.28. 2-methoxypyridine is a liquid with limited solubility in water. 2-methoxypyridine is hydrophobic in the neutral form, with an estimated log P of approximately 1.3 (similar to pyridine). When added to a strong acid solution, 2-methoxypyridine is protonated to form a highly soluble 2-methoxypyridinium salt; the pH varies over the range of 1 to 4 depending on the proportion of 2-methoxypyridine to acid used.

Pyridazine is a heterocyclic organic base having a pKa of 2.33. Pyridazine is a liquid that is miscible with water at all ratios. In contrast to pyridine, pyridazine is hydrophilic in the neutral form, with an estimated log P of approximately −0.7. When added to a strong acid solution, pyridazine is protonated to form a pyridazinium salt; the pH varies over the range of 1 to 3 depending on the proportion of pyridazine to acid used.

Adenine (6-aminopurine) is a purine derivative having a pKa of 4.15. Adenine is a solid that forms soluble salts with strong acids, e.g., perchloric and triflic acids.

Aniline (phenylamine, aminobenzene) is an organic compound with a pKa of 4.19. Aniline is a hydrophobic liquid that reacts with strong acids to form anilinium (phenylammonium) ions and that forms soluble salts with strong acids, e.g., triflic acid.

In some embodiments, a weak base and a strong acid are used to produce a weak base salt. As used herein, the term "strong acid" refers to an acid that ionizes (e.g., in an aqueous solution) completely by losing one proton, e.g., in some embodiments, a strong acid is an acid that is stronger in aqueous solution than a hydronium ion—accordingly, in some embodiments, strong acids are acids with a pKa less than approximately −1.74. In addition, the term "strong acid" as used herein refers to acids that dissociate nearly completely in very dilute solution though they may or may not be more acidic than hydronium ion. The term "strong acid" as used herein refers also to extremely strong acids (e.g., fluoroantimonic acid, triflic acid) and superacids that protonate water to give ionic, crystalline hydronium "salts", e.g., fluoroantimonic acid, magic acid, and perchloric acid. Accordingly, non-limiting examples of strong acids are, e.g., sulfuric acid (first dissociation only), hydrochloric acid, nitric acid, hydrobromic acid, hydroiodic acid, triflic acid, perchloric acid, bromic acid, perbromic acid, iodic acid, periodic acid, and sulfonic acids (organic oxyacids) such as, e.g., methanedisulfonic acid, methanesulfonic acid, p-toluenesulfonic acid (tosylic acid), 1,2-ethanedisulfonic acid ("edisylate"), and 1,3-propanedisulfonic acid ("eprodisate").

In particular embodiments, the strong acid is a diprotic acid having both first and second pKa values less than zero. Furthermore, it is contemplated that minimizing the molecular weight of the acid and maximizing the polarity of the acid provides additional guidance for selecting a suitable acid for embodiments of the technology.

Embodiments relate to the use of a weak base. As used herein, a weak base is a chemical base that does not completely ionize (e.g., in an aqueous solution), e.g., a chemical base that is partially protonated (e.g., in an aqueous solution).

Embodiments relate to the use of a weak base salt, e.g., a salt produced by the ionization of a weak base, e.g., by a strong acid.

In particular embodiments, a composition comprising liposomes is made using a weak base salt solution having a pH of at least 2, e.g., to allow for swelling of phospholipid (e.g., dipalmitoylphosphatidylcholine) during incubation (e.g., at 35 to 55° C., e.g., approximately 40° C., e.g., 42° C.). It is further preferred that the pH of the weak base salt solution is below the pKa of the weak base to limit the amount of free base in the solution, thus stabilizing the liposome membranes. In some embodiments, liposomes are prepared in the base salt solution and excess weak base is eliminated by standard washing techniques (e.g., sedimentation in a centrifuge, dialysis, gel chromatography, etc.). Then, a drug, bioactive agent, pharmaceutical agent, etc. is added to the composition comprising liposomes. Incubating the composition comprising the drug and the liposomes for a period of at least 30 minutes to 72 hours (e.g., at least 30 minutes, 1 hour, 1.5 hours, 2 hours, 2.5 hours, 3.0 hours, 3.5 hours, 4 hours, 4.5 hours, 5 hours, 12 hours, 24 hours, 48 hours, 72 hours or from 6 hours to 24 hours, 12 hours to 24 hours, 24 to 48 hours, 6 hours to 72 hours, 12 hours to 72 hours or 24 to 72 hours) produces a composition comprising liposomes loaded with the drug (e.g., the drug moves into the liposomes (e.g., into the intraliposomal space)). Manipulation and control of the extraliposomal (e.g., bulk) phase pH provides for control of drug loading (e.g., to maximize loading (e.g., to maximize efficiency of drug loading)). For example, in some embodiments a buffer is provided in the extraliposomal phase to control the extraliposomal pH. For example, in some embodiments a buffer is added to particular compositions to maintain the extraliposomal pH at a value at which the drug to be loaded is predominantly in the protonated (e.g., charged) form. For example, for drugs that are weak bases, the protonated form is a charged form.

In some embodiments, the preferable external loading pH for pyridine salts is 6 to 8; further, in some embodiments, the external loading pH is lower than 6 for compositions comprising 2-methoxypyridine or pyridazine (but greater than the pKa of the 2-methoxypyridine or pyridazine).

During the development of the technology described herein, experiments were performed indicating that the drugs chloroquine, doxycycline, hydromorphone, naltrexone, and buprenorphine are loaded into liposomes with high efficiency using one or more weak base compounds (e.g., pyridine, 2-methoxypyridine, pyridazine) In particular, loading liposomes using a weak base provided an improved (e.g., increased, e.g., high) loading efficiency and an improved (e.g., reduced, e.g., very low) in vitro leakage of the drug from the liposomes in the early phase of leakage (0 to 48 hours). The data collected indicated that liposome loading with a weak base is much improved to liposomes loaded using ammonium sulfate loading. In some embodiments, leakage of the loading base itself is quite rapid during the first few days. Thus, in some embodiments the weak loading bases act as sacrificial leakage agents, thereby eliminating the early phase loss of drug from liposomes. That is, in the early rapid phase of leakage from loaded liposomes, the weak base leaks from the liposomes in lieu of the drug leaking from the liposomes, thus maintaining a high amount of drug inside the liposomes.

Pharmaceutical Preparations

In some embodiments, liposome compositions prepared by the methods described herein are administered alone or in a mixture with a physiologically-acceptable carrier (such as physiological saline or phosphate buffer) selected in accordance with the route of administration and standard pharmaceutical practice. Generally, normal saline is employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. In compositions comprising saline or other salt-containing carriers, the carrier is preferably added following liposome formation. Thus, after the liposome is formed and loaded with a suitable drug, the liposome can be diluted into pharmaceutically acceptable carriers such as normal saline. These compositions may be sterilized by conventional, well-known sterilization techniques. The resulting aqueous solutions may be packaged for use or filtered under aseptic conditions and lyophilized, the lyophilized preparation being combined with a sterile aqueous solution prior to administration. The compositions may also contain pharmaceutically acceptable auxiliary substances as required to approximate physiological conditions, such as pH-adjusting and buffering agents, tonicity adjusting agents and the like, for example, sodium acetate, sodium lactate, sodium chloride, potassium chloride, calcium chloride, etc.

Additionally, the composition may include lipid-protective agents that protect lipids against free-radical and lipid-peroxidative damages on storage. Lipophilic free-radical quenchers, such as alpha-tocopherol and water-soluble iron-specific chelators, such as ferrioxamine, are suitable.

The concentration of liposomes in the pharmaceutical formulations can vary widely, e.g., from less than approximately 0.05%, usually at least approximately 2 to 5% to as much as 10 to 30% by weight and are selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, liposomes composed of irritating lipids may be diluted to low concentrations to lessen inflammation at the site of administration. The amount of liposomes administered will depend upon the particular drug used, the disease state being treated and the judgment of the clinician but will generally be between approximately 0.01 and approximately 50 mg per kilogram of body weight, preferably between approximately 0.1 and approximately 5 mg per kg of body weight.

In some embodiments, it is desirable to include polyethylene glycol (PEG)-modified phospholipids, PEG-ceramide, or ganglioside $G_{M1}$-modified lipids to the liposomes. Addition of such components prevents liposome aggregation and provides for increasing circulation lifetime and increasing the delivery of the loaded liposomes to the target tissues. Typically, the concentration of the PEG-modified phospholipids, PEG-ceramide, or $G_{M1}$-modified lipids in the liposome will be approximately 1 to 15%.

In some embodiments, overall liposome charge is an important determinant in liposome clearance from the blood. Charged liposomes are typically taken up more rapidly by the reticuloendothelial system (Juliano, Biochem. Biophys. Res. Commun. 63: 651 (1975)) and thus have shorter half-lives in the bloodstream. Liposomes with prolonged circulation half-lives are typically desirable for therapeutic and certain diagnostic uses. For instance, liposomes that are maintained from 8, 12, or up to 24 hours in the bloodstream are particularly preferred.

In another example of their use, drug-loaded liposomes can be incorporated into a broad range of topical dosage forms including but not limited to gels, oils, emulsions, and the like. For instance, in some embodiments the suspension containing the drug-loaded liposomes is formulated and administered as a topical cream, paste, ointment, gel, lotion, and the like.

The present technology also provides liposome compositions in kit form. The kit will typically comprise a container that is compartmentalized for holding the various elements of the kit. The kit contains the compositions of the present inventions, preferably in dehydrated form, with instructions for their rehydration and administration.

In still other embodiments, the drug-loaded liposomes have a targeting moiety attached to the surface of the liposome. Methods of attaching targeting moieties (e.g., antibodies, proteins) to lipids (such as those used in the present particles) are known to those of skill in the art.

Dosage for the drug-loaded liposome formulations depends on the ratio of drug to lipid and the administrating physician's and/or veterinarian's opinion based on age, weight, and condition of the patient.

In some embodiments, compositions comprising liposomes encapsulating a bioactive agent are formulated with a buffering agent. The buffering agent may be any pharmaceutically acceptable buffering agent. Buffer systems include citrate buffers, acetate buffers, borate buffers, and phosphate buffers. Examples of buffers include citric acid, sodium citrate, sodium acetate, acetic acid, sodium phosphate and phosphoric acid, sodium ascorbate, tartaric acid, maleic acid, glycine, sodium lactate, lactic acid, ascorbic acid, imidazole, sodium bicarbonate and carbonic acid, sodium succinate and succinic acid, histidine, and sodium benzoate and benzoic acid.

In some embodiments, compositions comprising liposomes encapsulating a bioactive agent are formulated with a chelating agent. The chelating agent may be any pharmaceutically acceptable chelating agent. Chelating agents include ethylene diaminetetraacetic acid (also synonymous with EDTA, edetic acid, versene acid, and sequestrene), and EDTA derivatives, such as dipotassium edetate, disodium edetate, edetate calcium disodium, sodium edetate, trisodium edetate, and potassium edetate. Other chelating agents include citric acid and derivatives thereof. Citric acid also is known as citric acid monohydrate. Derivatives of citric acid include anhydrous citric acid and trisodiumcitrate-dihydrate. Still other chelating agents include niacinamide and derivatives thereof and sodium deoxycholate and derivatives thereof.

In some embodiments, compositions comprising liposomes encapsulating a bioactive agent are formulated with an antioxidant. The antioxidant may be any pharmaceutically acceptable antioxidant. Antioxidants are well known to those of ordinary skill in the art and include materials such as ascorbic acid, ascorbic acid derivatives (e.g., ascorbylpalmitate, ascorbylstearate, sodium ascorbate, calcium ascorbate, etc.), butylated hydroxy anisole, buylated hydroxy toluene, alkylgallate, sodium meta-bisulfate, sodium bisulfate, sodium dithionite, sodium thioglycollic acid, sodium formaldehyde sulfoxylate, tocopherol and derivatives thereof, (d-alpha tocopherol, d-alpha tocopherol acetate, dl-alpha tocopherol acetate, d-alpha tocopherol succinate, beta tocopherol, delta tocopherol, gamma tocopherol, and d-alpha tocopherol polyoxyethylene glycol 1000 succinate) monothioglycerol, and sodium sulfite. Such materials are typically added in ranges from 0.01 to 2.0%.

In some embodiments, compositions comprising liposomes encapsulating a bioactive agent are formulated with a cryoprotectant. The cryoprotecting agent may be any pharmaceutically acceptable cryoprotecting agent. Common cryoprotecting agents include histidine, polyethylene glycol, polyvinyl pyrrolidine, lactose, sucrose, mannitol, and polyols.

In some embodiments, compositions comprising liposomes encapsulating a bioactive agent are formulated with an isotonicity agent. The isotonicity agent can be any pharmaceutically acceptable isotonicity agent. This term is used in the art interchangeably with iso-osmotic agent, and is known as a compound that is added to the pharmaceutical preparation to increase the osmotic pressure, e.g., in some embodiments to that of 0.9% sodium chloride solution, which is iso-osmotic with human extracellular fluids, such as plasma. Preferred isotonicity agents are sodium chloride, mannitol, sorbitol, lactose, dextrose and glycerol.

Compositions of the liposomes encapsulating a bioactive agent may optionally comprise a preservative. Common preservatives include those selected from the group consisting of chlorobutanol, parabens, thimerosol, benzyl alcohol, and phenol. Suitable preservatives include but are not limited to: chlorobutanol (0.3-0.9% w/v), parabens (0.01-5.0%), thimerosal (0.004-0.2%), benzyl alcohol (0.5-5%), phenol (0.1-1.0%), and the like.

In some embodiments, compositions comprising liposomes encapsulating a bioactive agent are formulated with a humectant to provide a pleasant mouth-feel in oral applications. Humectants known in the art include cholesterol, fatty acids, glycerin, lauric acid, magnesium stearate, pentaerythritol, and propylene glycol.

In some embodiments, an emulsifying agent is included in the formulations, for example, to ensure complete dissolution of all excipients, especially hydrophobic components such as benzyl alcohol. Many emulsifiers are known in the art, e.g., polysorbate 60.

For some embodiments related to oral administration, it may be desirable to add a pharmaceutically acceptable flavoring agent and/or sweetener. Compounds such as saccharin, glycerin, simple syrup, and sorbitol are useful as sweeteners.

Administration and Therapy

Once the therapeutic agent has been loaded into the liposomes, the combination can be administered to a patient by a variety of techniques.

Preferably, the pharmaceutical compositions are administered parenterally, e.g., intraarticularly, intravenously, intraperitoneally, subcutaneously, or intramuscularly. In some embodiments, the pharmaceutical compositions are administered intravenously or intraperitoneally by a bolus injection. For example, see Raham et al., U.S. Pat. No. 3,993,754; Sears, U.S. Pat. No. 4,145,410; Papahadjopoulos et al., U.S. Pat. No. 4,235,871; Schneider, U.S. Pat. No. 4,224,179; Lenk et al., U.S. Pat. No. 4,522,803; and Fountain et al., U.S. Pat. No. 4,588,578. Particular formulations that are suitable for this use are found in Remington's Pharmaceutical Sciences, Mack Publishing Company, Philadelphia, Pa., 17th ed. (1985). Typically, the formulations comprise a solution of the liposomes suspended in an acceptable carrier, preferably an aqueous carrier. A variety of aqueous carriers are used in embodiments of the technology, e.g., water, buffered water, 0.9% isotonic saline, and the like. These compositions may be sterilized by conventional, well-known sterilization techniques, or may be sterile filtered. The resulting aqueous solutions may be packaged for use as is, or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

Dosage for the liposome formulations will depend on the ratio of drug to lipid and the administrating physician's opinion based on age, weight, and condition of the patient.

The methods of the present invention may be practiced in a variety of hosts. Preferred hosts include mammalian species, such as humans, non-human primates, dogs, cats, cattle, horses, sheep, and the like.

In other methods, the pharmaceutical preparations may be contacted with the target tissue by direct application of the preparation to the tissue. The application may be made by topical, "open", or "closed" procedures. By "topical", it is meant the direct application of the pharmaceutical preparation to a tissue exposed to the environment, such as the skin, oropharynx, external auditory canal, and the like. "Open" procedures are those procedures include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue. "Closed" procedures are invasive procedures in which the internal target tissues are not directly visualized, but accessed via inserting instruments through small wounds in the skin. For example, the preparations may be administered to the peritoneum by needle lavage. Likewise, the pharmaceutical preparations may be administered to the meninges or spinal cord by infusion during a lumbar puncture followed by appropriate positioning of the patient as commonly practiced for spinal anesthesia or metrizamide imaging of the spinal cord. Alternatively, the preparations may be administered through endoscopic devices.

The compositions of the present invention that further comprise a targeting antibody on the surface of the liposome are particularly useful for the treatment of certain diseases.

The therapeutic use of liposomes can include the delivery of drugs that are normally toxic in the free form. In the liposomal form, the toxic drug may be directed away from the sensitive tissue where toxicity can result and targeted to selected areas where they can exert their therapeutic effects. Liposomes can also be used therapeutically to release drugs slowly, over a prolonged period of time, thereby reducing the frequency of drug administration through an enhanced pharmacokinetic profile. In addition, liposomes can provide a method for forming an aqueous dispersion of hydrophobic drugs for intravenous delivery.

The route of delivery of liposomes can also affect their distribution in the body. Passive delivery of liposomes involves the use of various routes of administration e.g., parenterally, although other effective administration forms, such as intraarticular injection, inhalant mists, orally active formulations, transdermal iotophoresis, or suppositories are also envisioned. Each route produces differences in localization of the liposomes.

Because dosage regimens for pharmaceutical agents are well known to medical practitioners, the amount of the liposomal pharmaceutical agent formulations that is effective or therapeutic for the treatment of a disease or condition in mammals and particularly in humans will be apparent to those skilled in the art. The optimal quantity and spacing of individual dosages of the formulations herein will be determined by the nature and extent of the condition being treated, the form, route and site of administration, and the particular patient being treated, and such optima can be determined by conventional techniques. It will also be appreciated by one of skill in the art that the optimal course of treatment, e.g., the number of doses given per day for a defined number of days, can be ascertained by those skilled in the art using conventional course of treatment determination tests.

The liposomes containing therapeutic agents and the pharmaceutical formulations thereof of the present technology and those produced by the processes thereof can be used therapeutically in animals (including man) in the treatment of infections or conditions which require: (1) repeated administrations, (2) the sustained delivery of the drug in its bioactive form, or (3) the decreased toxicity with suitable efficacy compared with the free drug in question.

The mode of administration of the liposomes containing the pharmaceutical agents and the pharmaceutical formulations thereof determine the sites and cells in the organism to which the compound will be delivered. The liposomes of the present technology can be administered alone but will generally be administered in admixture with a pharmaceutical carrier selected with regard to the intended route of administration and standard pharmaceutical practice. The preparations may be injected parenterally, for example, intravenously. For parenteral administration, they can be used, for example, in the form of a sterile aqueous solution that may contain other solutes, for example, enough salts or glucose to make the solution isotonic.

For the oral mode of administration, the liposomal therapeutic drug formulations of this technology can be used in the form of tablets, capsules, lozenges, troches, powders, syrups, elixirs, aqueous solutions and suspensions, and the like. In the case of tablets, carriers that can be used include lactose, sodium citrate, and salts of phosphoric acid. Various disintegrants, such as starch, and lubricating agents, such as magnesium stearate, sodium lauryl sulfate and talc, are commonly used in tablets. For oral administration in capsule form, useful diluents are lactose and high molecular weight polyethylene glycols. When aqueous suspensions are required for oral use, the active ingredient is combined with emulsifying and suspending agents. If desired, certain sweetening and/or flavoring agents can be added.

For the topical mode of administration, the liposome-drug formulations of the present technology may be incorporated into dosage forms such as gels, oils, emulsions, and the like. Such preparations may be administered by direct application as a cream, paste, ointment, gel, lotion or the like.

For administration to humans in the curative, remissive, retardive, or prophylactic treatment of diseases the prescribing physician will ultimately determine the appropriate dosage of the drug for a given human subject, and this can be expected to vary according to the age, weight, and response of the individual as well as the nature and severity of the patient's disease. The dosage of the drug in liposomal form will generally be approximately that employed for the free drug. In some cases, however, it may be necessary to administer dosages outside these limits and, in some embodiments, the technology comprises administering dosages in excess of these limits due to the extended-release characteristics of the formulations.

The term "therapeutically effective" as it pertains to the compositions of the invention means that a biologically active substance present in the aqueous component within the vesicles is released in a manner sufficient to achieve a particular medical effect for which the therapeutic agent is intended. Examples, without limitation, of desirable medical effects that can be attained are chemotherapy, antibiotic therapy, and regulation of metabolism. Exact dosages will vary depending upon such factors as the particular therapeutic agent and desirable medical effect, as well as patient factors such as age, sex, general condition, and the like. Those of skill in the art can readily take these factors into account and use them to establish effective therapeutic concentrations without resort to undue experimentation.

Generally, however, the dosage range appropriate for human use includes the range of 0.1 to 6000 mg/m$^2$ of body surface area. For some applications, such as intravenous administration, the dose required may be quite small, but for other applications, such as subcutaneous and/or intraperitoneal administration, the dose desired to be used may be very large. While doses outside the foregoing dose range may be given, this range encompasses the breadth of use for practically all the biologically active substances.

The liposomes may be administered for therapeutic applications by any desired route, for example, intramuscular, intraarticular, epidural, intrathecal, intraperitoneal, subcutaneous, intravenous, intralymphatic, oral and submucosal, and by implantation under many different kinds of epithelia, including the bronchialar epithelia, the gastrointestinal epithelia, the urogenital epithelia, and various mucous membranes of the body.

In addition, the liposomes of the invention can be used to encapsulate compounds useful in agricultural applications, such as fertilizers, pesticides, and the like. For use in agriculture, the liposomes can be sprayed or spread onto an area of soil where plants will grow and the agriculturally effective compound contained in the vesicles will be released at a controlled rate by contact with rain and irrigation waters. Alternatively the slow-releasing vesicles can be mixed into irrigation waters to be applied to plants and crops. One skilled in the art will be able to select an effective amount of the compound useful in agricultural applications to accomplish the particular goal desired, such as the killing of pests, the nurture of plants, etc.

During the development of embodiments of the technology provided, experiments were conducted to collect data relevant to the in vivo use of the liposome preparations and delivery of pharmaceuticals to a subject. See, e.g., Example 9. In particular, during the experiments a pharmaceutical (e.g., buprenorphine) was loaded into liposomes according to embodiments of the technology provided herein, e.g., using a weak base (e.g., 2-methoxypyridinium sulfate and/or 2-methoxypyridinium eprodisate). Data collected indicated that weak base loading provides therapeutically significant serum concentrations of the pharmaceutical for a longer in vivo period of time than the period of time that therapeutically significant serum concentrations of the pharmaceutical are provided by present techniques such as acid loading. Furthermore, the data indicated that the technology (e.g., the use of eprodisate) provides serum concentrations of the pharmaceutical during the first two weeks after administration that are lower than the serum concentrations of the pharmaceutical when administered using present technologies. In particular, present technologies generally provide serum concentrations of pharmaceuticals that are higher than needed to provide an effect, thus resulting in inefficient use of the pharmaceutical and/or providing the pharmaceutical a level that produces undesired side effects associated with unnecessarily elevated dosages. Accordingly, the technology described herein provides an improved effective dose of a pharmaceutical (e.g., the dose is not too high and/or the dose is not higher than is needed to provide an effect) relative to present technologies.

Although the disclosure herein refers to certain illustrated embodiments, it is to be understood that these embodiments are presented by way of example and not by way of limitation.

EXAMPLES

During the development of embodiments of the technologies described herein, experiments were conducted to evaluate the loading of drugs into liposomes using weak loading bases as described herein. In particular, data were collected to measure the efficiency of drug loading into liposomes loaded with a weak loading base and data were collected to measure drug and loading base leakage from the loaded liposomes into the extraliposomal space.

Methods

Spectrophotometric Analysis. Concentrations of loading bases and drugs loaded were measured using characteristic UV spectra and known absorbances at defined wavelengths. To determine the concentrations of the drug and the loading base in compositions comprising both the drug and the loading base, readings at two wavelengths were used and the concentrations of the drug and the loading base were solved using simultaneous equations. Reference values for the extinction coefficients of each substance at both reference wavelengths were determined.

Liposome Preparation. A mixture containing 80 µmol dipalmitoylphosphatidylcholine (DPPC) and 40 µmol cholesterol (chol) was dried from a chloroform solution using a rotary evaporator. The lipid mixture was resuspended in 1 mL of tert-butanol, transferred to a 16-mm screw cap tube and frozen in a slurry of dry ice and 2-propanol. The tube was placed in a lyophilizer flask and freeze dried for 24 hours to produce a microporous lipid lyophilizate. Lipid lyophilizates were stored at −20° C. until use. Prior to liposome preparation, the lipid lyophilizate was removed from the freezer and allowed to warm to 22° C. A 1-mL aliquot of loading base solution was added to the lipid lyophilizate and the mixture was swollen in a water bath at 55° C. for 10 minutes to form liposomes. To eliminate the excess loading base, the liposome suspension was cooled to 22° C., diluted with isotonic NaCl, and sedimented at 300×g for 10 minutes. After aspiration of the supernatant, the pellet was resuspended two times in isotonic NaCl followed by sedimentation at 300×g for 10 minutes. The final liposome pellet was resuspended in 1 mL of an appropriate loading medium. Various buffer choices were used for the loading medium as indicated below for the specific drug to be loaded in each experiment. Then, a sample was solubilized with 1:3:1 v/v/v chloroform:methanol:water and analyzed spectrophotometrically to measure loading base content. Drug for loading was added to the suspension and incubated at 22° C. for 20 hours. Unencapsulated drug and released loading base were removed by diluting the solution 3 times with 8 mL of isotonic NaCl followed by sedimentation at 300×g for 10 minutes. After the third wash, the liposome pellet was suspended in isotonic NaCl solution. An aliquot of the suspension was removed from each preparation and solubilized in 1:3:1 v/v/v chloroform:methanol:water, and the amounts of drug and loading base in the liposomes were quantified spectrophotometrically.

Liposome Leakage, Dialysis Method. A 0.5-mL aliquot of liposome suspension was placed in a section of dialysis tubing tied at one end. The tubing was tied at the other end to form a sealed bag. The bag was placed in 4.5 mL of isotonic NaCl saline solution and placed on an orbital shaker. At specific time points, the dialysis bags were exchanged into fresh isotonic NaCl and the drug and loading base were quantified spectophotometrically in the external dialysis solutions.

Liposome Leakage, Sedimentation Method. Liposome samples were diluted to 3-5 mL and left on an orbital shaker at 22° C. At specific time points, the liposomes were sedimented in a centrifuge at 300×g for 5 minutes and an aliquot of the clear supernatant was analyzed spectrophotometrically for drug and loading base content. After measurement, the solution was returned to the liposome suspension, which was vortexed and returned to the orbital shaker.

Example 1: Chloroquine

During the development of embodiments of the technology provided herein, experiments were conducted to assess the loading of a chloroquine into liposomes using weak loading bases, e.g., pyridinium sulfate and pyridinium chloride.

Example 1a: Chloroquine Loaded Using 0.5 M Pyridinium Sulfate

Loading base solution: 0.5 M pyridinium sulfate (1 M with respect to pyridine).
Loading medium: 220 mM tris-nitrate buffer, pH 8.3.
Base content prior to drug loading: 26.7 µmol base per 80 µmol DPPC. 6.7 µmol per loading.
Loading efficiency: Loading of 2.5 µmol and 5 µmol chloroquine was close to 100% (Table 1). Based on the amount loaded when either 10 or 20 µmol of chloroquine was added, the loading capacity was approximately 9.5 µmol.

TABLE 1

Loading of chloroquine into liposomes with 0.5M pyridinium sulfate

| chloroquine added (µmol) | chloroquine captured (%) |
|---|---|
| 20 | 55.95 |
| 10 | 96.32 |
| 5 | 99.84 |
| 2.5 | 99.83 |

Figure 2:
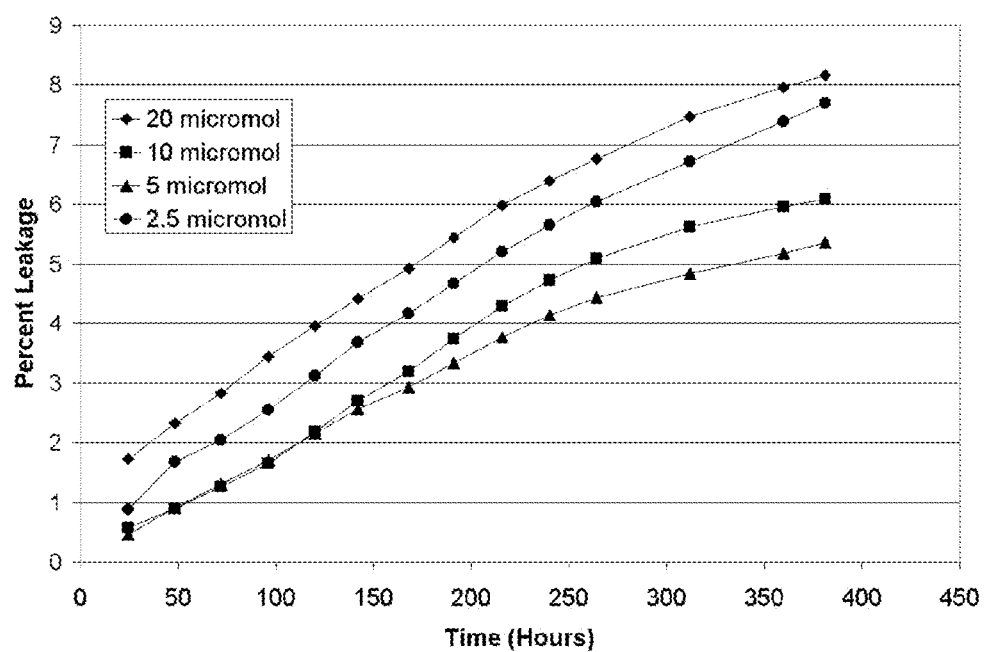
FIG. 2 is a plot showing leakage of chloroquine from 0.5 M pyridinium sulfate-containing, chloroquine-loaded liposomes.
Figure 3:
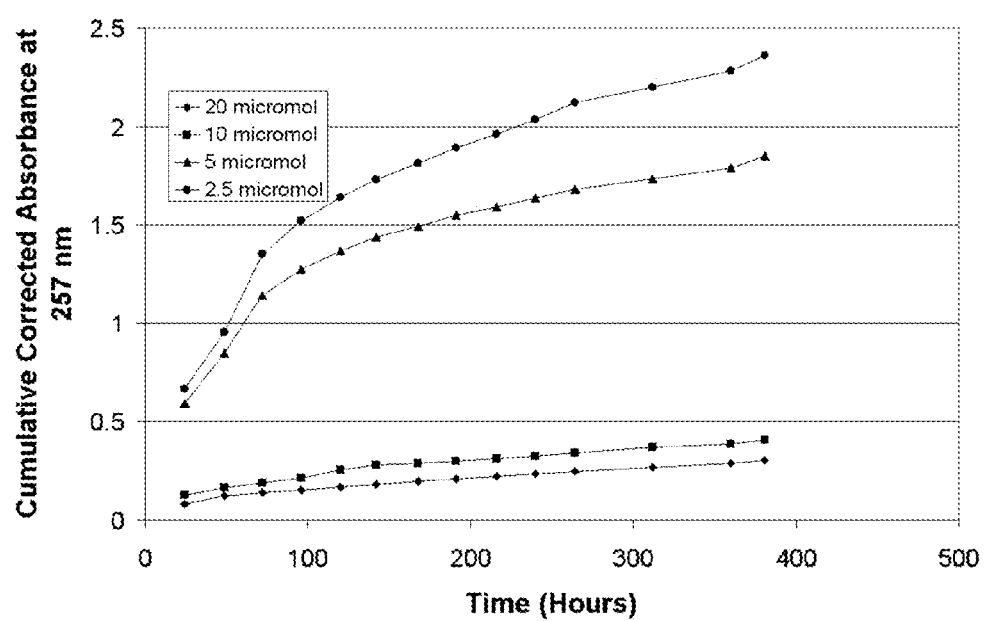
FIG. 3 is a plot showing leakage of pyridine from 0.5 M pyridinium sulfate-containing, chloroquine-loaded liposomes.

Leakage: Leakage of chloroquine (FIG. 2) and pyridine (FIG. 3) from liposomes was followed using the dialysis method. The 2.5-µmol and 5-µmol chloroquine preparations show leakage that is linear without an initial rapid phase of leakage (FIG. 2). The other preparations of liposomal chloroquine show some elevated leakage in the first 24 hours, though the amount is low (e.g., approximately 0.5 to 2%) (FIG. 2). Long-term chloroquine leakage rates are approximately 0.36% per day (FIG. 2). Based on previous results for ammonium sulfate-loaded liposomes, these small amounts of leakage are consistent with in vivo release times of at least 3 to 4 weeks in mammals. In contrast, pyridine leakage from the liposomes was initially very rapid for the liposomes loaded with 2.5 or 5 µmol of chloroquine and slower after 3 days (FIG. 3). This suggests that during the early phase of leakage, pyridine rather than chloroquine is lost from these liposomes. Thus, pyridine acts as a sacrificial leakage agent. Pyridine loss from liposomes loaded with 10 or 20 µmol of chloroquine was minimal (FIG. 3), indicating that most of the pyridine is displaced from these liposomes in the process of chloroquine loading.

Example 1b: Chloroquine Loaded Using 1 M Pyridinium Chloride

Loading base solution: 1 M pyridinium chloride (1 M with respect to pyridine).
Loading medium: 220 mM tris-nitrate buffer, pH 8.3.
Base content prior to drug loading: 30.2 mol per 80 µmol DPPC. 7.5 µmol per loading.
Loading efficiency: Loading efficiency of 2.5 or 5 µmol chloroquine was close to 100% (Table 2). Based on the amount loaded when either 10 or 20 µmol of chloroquine was added, the loading capacity was approximately 8 µmol.

TABLE 2

Loading of chloroquine into liposomes with 1M pyridinium chloride

| chloroquine added (µmol) | chloroquine captured (%) |
|---|---|
| 20 | 44.65 |
| 10 | 79.64 |
| 5 | 99.04 |
| 2.5 | 99.35 |

Figure 4:
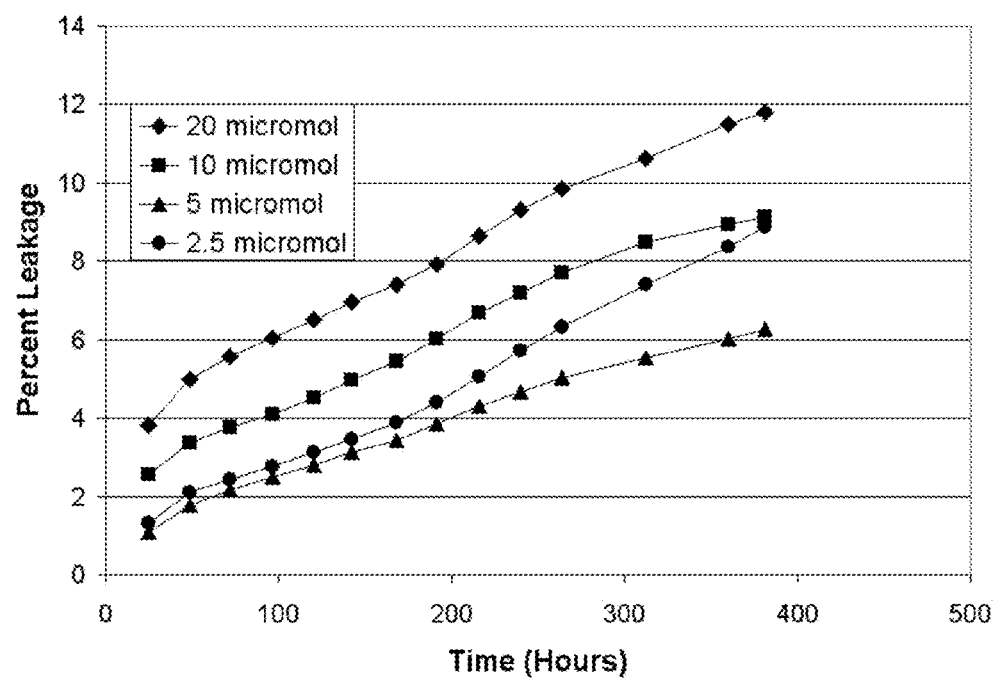
FIG. 4 is a plot showing leakage of chloroquine from 1 M pyridinium chloride-containing, chloroquine-loaded liposomes.
Figure 5:
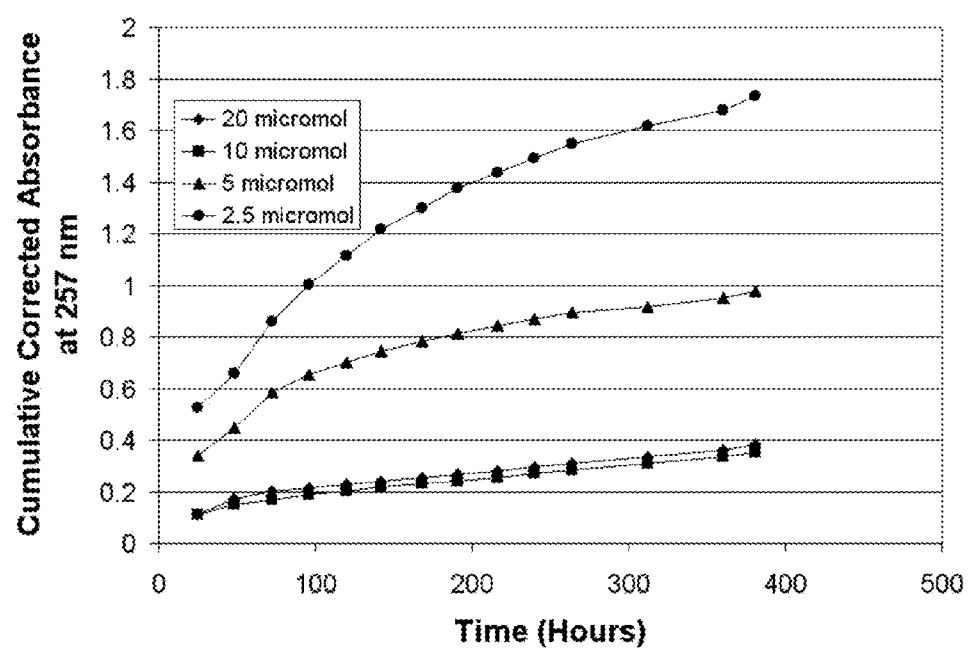
FIG. 5 is a plot showing leakage of pyridine from 1 M pyridinium chloride-containing, chloroquine-loaded liposomes.

Leakage. Leakage of chloroquine (FIG. 4) and pyridine (FIG. 5) from liposomes was followed using the dialysis method. The 2.5-µmol and 5-µmol preparations show chloroquine leakage that is linear without an initial rapid phase of leakage (FIG. 4). The other preparations of liposomal chloroquine show some elevated leakage in the first 24 hours, though the amount is low (approximately 2 to 4%) (FIG. 4). Long-term chloroquine leakage rates are approximately 0.55% per day (FIG. 4). Based on previous results for ammonium sulfate-loaded liposomes, these small amounts of leakage are consistent with in vivo release times of at least 3 to 4 weeks in mammals. In contrast, pyridine leakage from the liposomes was initially very rapid for the liposomes loaded with 2.5 or 5 µmol of chloroquine and slower after 3 days (FIG. 5). This suggests that during the early phase of leakage, pyridine rather than chloroquine is lost from these liposomes. Thus, pyridine acts as a sacrificial leakage agent. Pyridine loss from liposomes loaded with 10 or 20 µmol of chloroquine was minimal (FIG. 5), demonstrating that most of the pyridine is displaced from these liposomes in the process of chloroquine loading.

Comparison Example 1c: Chloroquine Loaded Using 0.133 M Ammonium Sulfate

During the development of embodiments of the technology provided herein, experiments were conducted to compare loading efficiency and leakage of liposomes loaded with drug according to the technology provided herein with liposomes loaded with drug according to existing (e.g., ammonium sulfate) methods.

Figure 6:
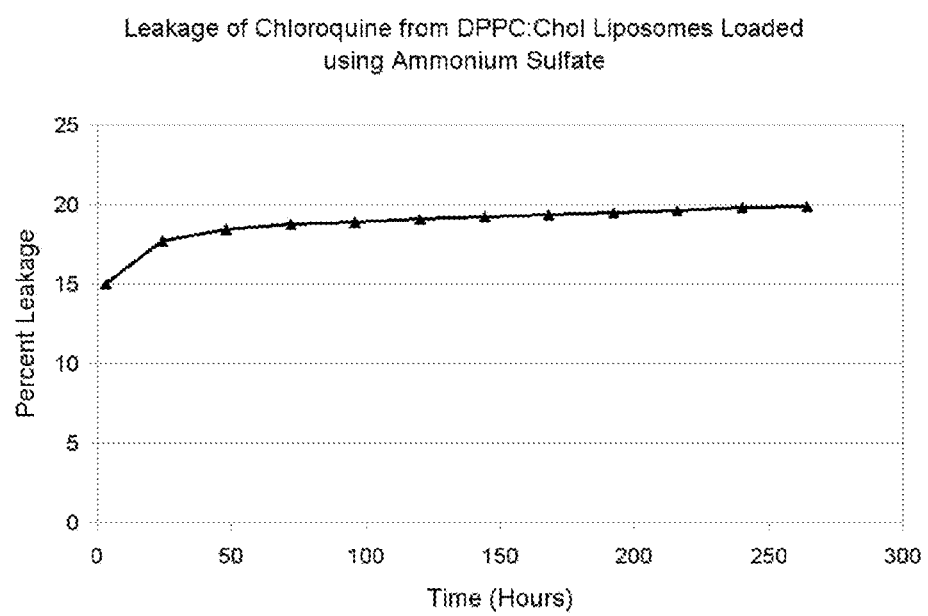
FIG. 6 is a plot showing leakage of chloroquine from 0.133 M ammonium sulfate-containing, chloroquine-loaded liposomes.

Leakage. As an indication of the improvements provided by the technology described herein, the results shown in Examples 1a and 1b were compared to the leakage of chloroquine from liposomes loaded using an existing ammonium sulfate gradient method. Leakage was followed using the dialysis method. The data indicated that the initial leakage from the liposomes was extensive and leakage accounted for 18% of the loaded drug in the first 24 hours (FIG. 6). The long-term leakage (e.g., after 72 hours) from these liposomes is comparable to that seen with the pyridinium sulfate-loaded liposomes shown above. Accordingly, the major differences for pyridinium sulfate loading are the quantitative loading efficiency and the elimination and/or minimization of rapid short-term leakage.

Example 2: Hydromorphone Loaded Using 0.5 M Pyridinium Sulfate

During the development of embodiments of the technology provided herein, experiments were conducted to assess the loading of a hydromorphone into liposomes using weak loading bases, e.g., pyridinium sulfate.

Loading base solution: 0.5 M pyridinium sulfate (1 M with respect to pyridine).

Loading medium: 220 mM tris-chloride buffer, pH 8.3.

Base content prior to drug loading: 121 µmol in 160 µmol DPPC. 24.58 µmol per loading Loading Efficiency: Loading efficiency of hydromorphone was 43 to 83% (Table 3), depending on the amount added. Based on the amount loaded when 48 µmol of hydromorphone was added, the loading capacity was approximately 20 µmol.

TABLE 3

| Loading of hydromorphone into liposomes with 0.5M pyridinium sulfate | |
|---|---|
| hydromorphone added (µmol) | hydromorphone captured (%) |
| 48 | 42.28 |
| 24 | 72.29 |
| 12 | 82.64 |
| 6 | 75.55 |

Figure 7:
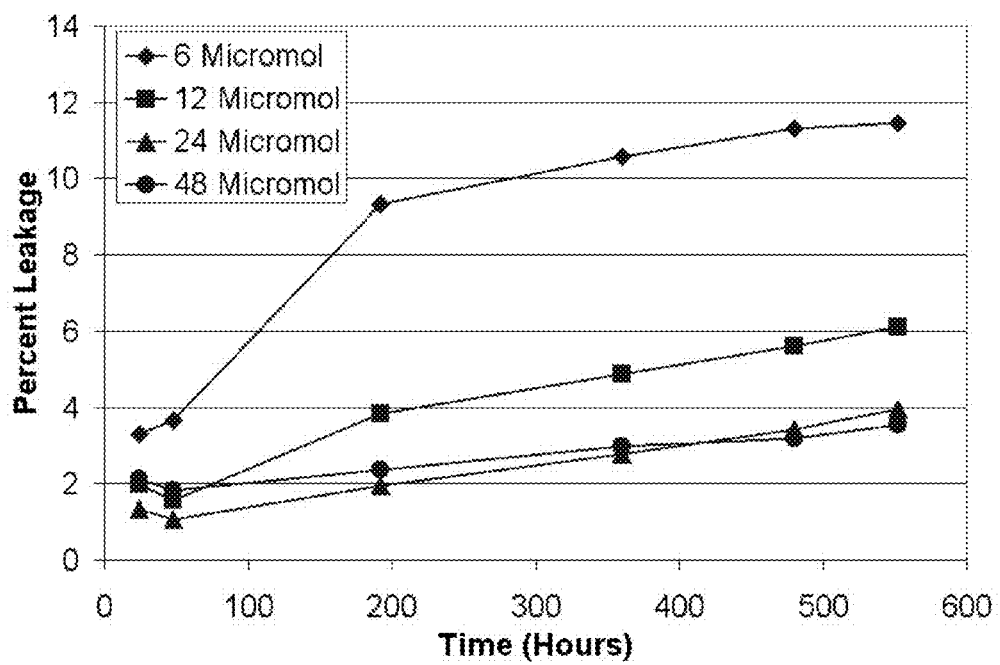
FIG. 7 is a plot showing leakage of hydromorphone from 0.5 M pyridinium sulfate-containing, hydromorphone-loaded liposomes.

Leakage. Leakage of hydromorphone (FIG. 7) and pyridine (FIG. 8) was followed using the sedimentation method. The leakage of hydromorphone from these liposomes following loading was very low, e.g., amounting to only 4 to 11% of the liposome contents after 550 hours (FIG. 7). The preparation containing the least drug (6 µmol) appears to give an initial burst of leakage, while all others release drug at a steady rate that is as low as 0.1% per day (FIG. 7).

Example 3: Loading of Naltrexone into Liposomes with 1.5 M Pyridinium Sulfate

During the development of embodiments of the technology provided herein, experiments were conducted to assess the loading of a naltrexone into liposomes using weak loading bases, e.g., pyridinium sulfate.

Loading base solution: 1.5 M pyridinium sulfate (3 M with respect to pyridine).

Loading medium: 220 mM tris-chloride buffer, pH 7.0, adjusted to pH 8.1

Base content prior to drug loading: 144 µmol per 80 µmol DPPC. 144 µmol per loading.

Loading efficiency: Loading efficiency for 50 µmol naltrexone was 91.7%. This is better than seen with hydromorphone and may reflect the higher amount of pyridine in the liposomes from using 1.5 M pyridinium sulfate.

Figure 8:
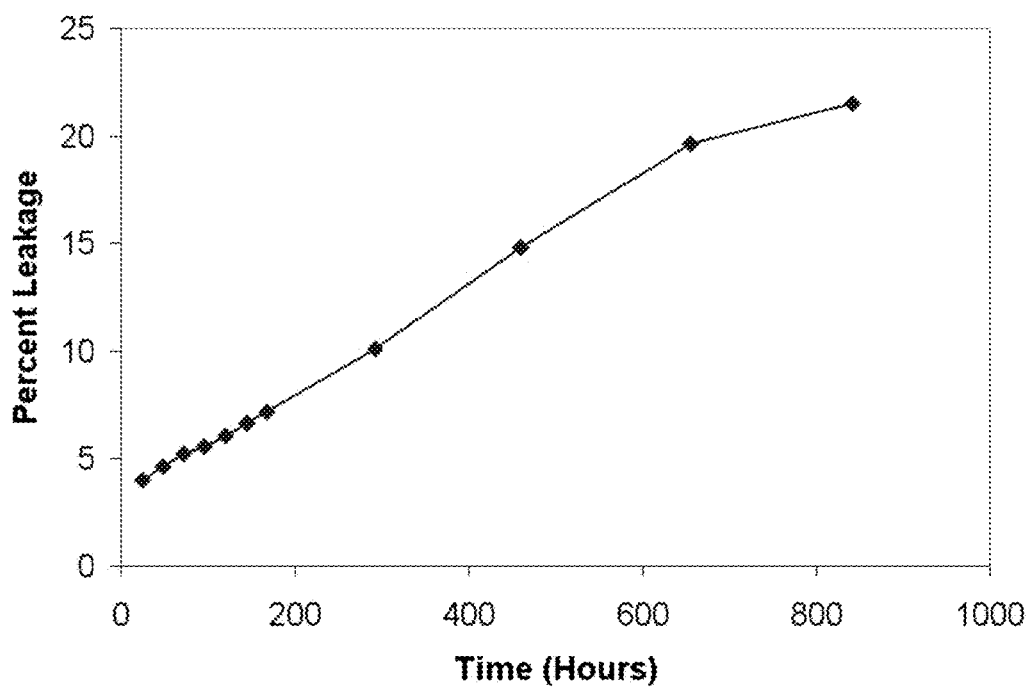
FIG. 8 is a plot showing leakage of naltrexone from 1.5 M pyridinium sulfate-containing, naltrexone-loaded liposomes.

Leakage. The loss of naltrexone from these liposomes following loading was followed using the sedimentation method (FIG. 8). The release of naltrexone was uniform as a function of elapsed time and occurred without an early rapid release rate, although there is an initial release of approximately 4% at 24 hours (FIG. 8). 20% of the liposome contents are released in 672 hours, a release rate of less than 1% per day (FIG. 8). This rate is faster than was seen for hydromorphone and may reflect the lower pKa of naltrexone (pKa 7.3) with respect to hydromorphone (pKa 7.8 to 8.9).

Example 4: Buprenorphine

During the development of embodiments of the technology provided herein, experiments were conducted to assess the loading of a buprenorphine into liposomes using weak loading bases, e.g., pyridinium sulfate, 2-methoxypyridinium sulfate, 2-methoxypyridinium triflate, and pyridazinium triflate.

Example 4a: Buprenorphine Loaded Using 1.5 M Pyridinium Sulfate

Loading base solution: 1.5 M pyridinium sulfate (3 M with respect to pyridine).

Loading medium: 200 mM sodium acetate buffer, pH 3.5 to 4.0.

Base content prior to drug loading: 92 µmol per 80 µmol DPPC. 92 µmol per loading.

Loading efficiency: Loading efficiency for 17.86 µmol buprenorphine was 44.47% (Table 5, Example 4a). Buprenorphine has quite limited solubility owing to its high hydrophobicity. Accordingly, the loading process was initiated by loading at pH 3.5 in acetate buffer and slowly increasing the pH to 4.0 as the loading progressed. These data indicate that, in some embodiments, efficient loading is provided by matching the physicochemical properties of the loading base (e.g., pyridine) and drug (e.g., buprenorphine). For example, while the data indicate that, in general, efficient loading using pyridine occurs at an extraliposomal pH of at least 7, buprenorphine has very limited solubility at this particular pH.

Leakage. The loss of buprenorphine from these liposomes following loading was followed using the sedimentation method (FIG. 9, Example 4a). 22% of the liposome contents were released after approximately 500 hours, although the initial release rate was faster with 17% release in the first 170 hours. This faster release rate may occur because buprenorphine is a very hydrophobic drug, e.g., buprenorphine has a log P of 4.3 compared with 1.3 for hydromorphone and naltrexone. This higher log P may indicate that an initial faster release of buprenorphine is not prevented by the sacrificial release of pyridine.

Example 4b: Buprenorphine Loaded Using 0.5 M 2-Methoxypyridinium Sulfate

Loading base solution: 0.5 M 2-methoxypyridinium sulfate (1 M with respect to 2-methoxypyridine).

Loading medium: 200 mM sodium acetate buffer, pH 3.5.

Base content prior to drug loading: 10.88 µmol per 80 µmol DPPC. 10.88 µmol per loading.

Loading efficiency: Loading efficiency for 9.9 µmol buprenorphine was 89.77% (Table 5, Example 4b). Surprisingly, this highly efficient loading occurred at pH 3.5, indicating the benefits of using 2-methoxypyridine for buprenorphine loading. Buprenorphine has quite limited solubility owing to its high hydrophobicity. Without being bound by theory, it was contemplated that the lower pKa of 2-methoxypyridine (3.28) would provide a lower intraliposomal pH prior to loading. Accordingly, a favorable pH gradient for drug loading exists even when the extraliposomal pH is only 3.5. Further, the residual 2-methoxypyridine in the liposomes prior to drug loading was quite low compared to the amount that was observed for liposomes containing a comparable concentration of pyridinium sulfate. Without being bound by theory, it is contemplated that a significant portion of the loss of 2-methoxypyridinium sulfate is due to conversion of sulfate ions to bisulfate, which has a pKa of 1.98.

Leakage. The loss of buprenorphine from these liposomes following loading was followed with the sedimentation method (FIG. 9, Example 4b). 3.95% of the liposome contents were released in the first 48 hours, while by 552 hours the total loss was 7.94%, a release rate of 0.35% per day. This rate is much slower than the leakage rate observed for buprenorphine loaded using pyridinium sulfate. The lower pKa of 2-methoxypyridine (3.28, compared to 5.3 for pyridine) provides a lower intraliposomal pH, which slows the release of buprenorphine. The residual 2-methoxypyridine may also be a more effective sacrificial release agent for buprenorphine than pyridine.

Example 4c: Buprenorphine Loaded Using 1 M 2-Methoxypyridinium Triflate

Loading base solution: 1 M 2-methoxypyridinium triflate (1 M with respect to 2-methoxypyridine).

Loading medium: 200 mM sodium citrate buffer, pH 3.5.

Base content prior to drug loading: 48.6 µmol per 80 µmol DPPC. 48.6 µmol per loading.

Loading efficiency: Loading efficiency for 9.9 µmol buprenorphine was 86.3% (Table 5, Example 4c). Surprisingly, this high loading efficiency occurred at pH 3.5, indicating again the benefit of using 2-methoxypyridine in preference to pyridine for buprenorphine loading, since it has quite limited solubility owing to its high hydrophobicity. The residual amount of 2-methoxypyridine in the liposomes was much higher than the residual amount of 2-methoxypyridinium sulfate observed in the previous experiments. Triflate has no pKa comparable to bisulfate, and therefore does not permit additional loss through the absorption of protons by the acid ion.

Figure 9:
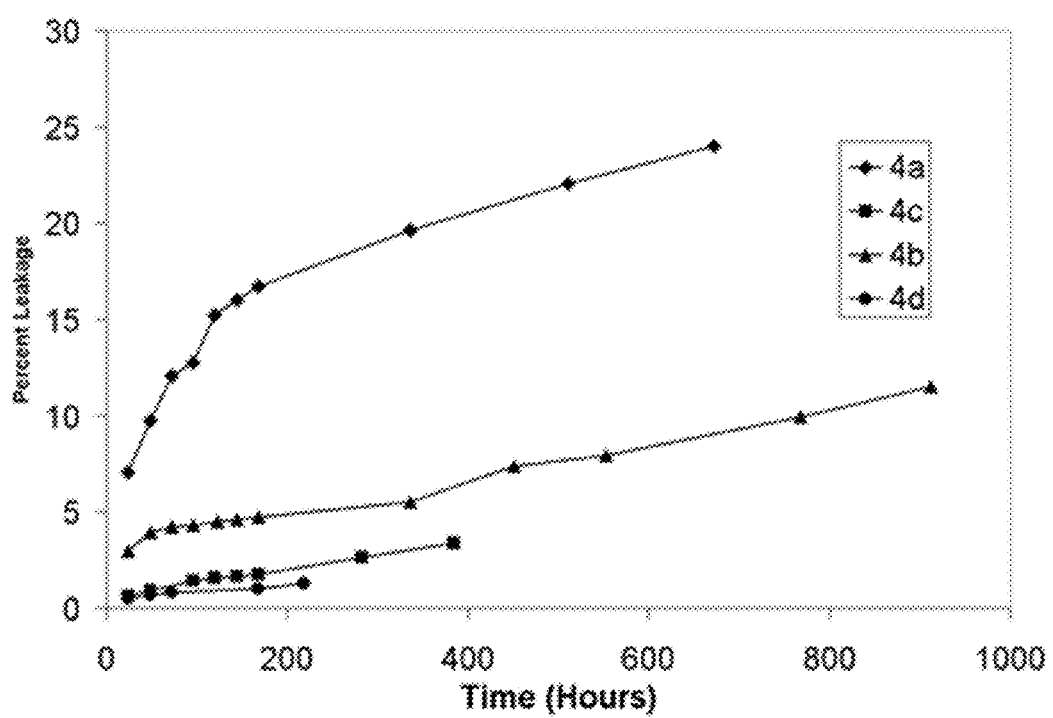
FIG. 9 is a plot showing leakage of buprenorphine from liposomes when the buprenorphine is loaded using pyridinium sulfate (diamonds), 2-methoxypyridinium sulfate (triangles), 2-methoxypyridinium triflate (squares), and pyridazinium triflate (circles).

Leakage. The loss of buprenorphine from these liposomes following loading was followed using the sedimentation method (FIG. 9, Example 4c). There is an initial release of 0.7% after 24 hours and a total release of 3.45% of the liposome contents in the first 384 hours, a release rate of 0.2% per day. While the initial release is lower, the rate after 168 hours is very similar to that seen for buprenorphine loaded using 2-methoxypyridinium sulfate. Therefore, while the higher retention of 2-methoxypyridine in the liposomes using this salt reduces initial leakage, the overall leakage rate is higher than the rate observed for 2-methoxypyridinium sulfate. It is contemplated that this reflects the lower long-term leakage with sulfate versus triflate.

Example 4d: Buprenorphine Loaded Using 1.6875 M Pyridazinium Triflate

Loading base solution: 1.6875 M pyridazinium triflate (1.6875 M with respect to pyridazine).

Loading medium: 200 mM sodium citrate buffer, pH 3.5.

Base content prior to drug loading: 22.1 µmol per 80 µmol DPPC. 22.1 µmol per loading.

Loading efficiency: Loading efficiency for 9.9 µmol buprenorphine was 90.82% (Table 5, Example 4d). As with 2-methoxypyridine, this high efficiency loading occurred at pH 3.5, showing the benefit of using a loading base having a pKa that is comparable to the pKa of pyridazine (2.33). The residual amount of pyridazine in the liposomes was lower than that observed for 2-methoxypyridinium triflate. Triflate has no pKa comparable to bisulfate, and therefore would not permit additional loss through the absorption of protons by the acid ion. However, it is contemplated that the lower pKa of pyridazine results in an intraliposomal pH low enough to protonate the phosphate of the DPPC.

Leakage. The loss of buprenorphine from these liposomes following loading was followed using the sedimentation method (FIG. 9, Example 4d). The release observed was very low: 1.04% leaked after 168 hours, a release rate of 0.14% per day.

TABLE 5

Loading of buprenorphine

| Example | buprenorphine added (µmol) | buprenorphine captured (%) |
|---|---|---|
| 4a | 17.86 | 44.47 |
| 4b | 9.91 | 89.77 |
| 4c | 9.91 | 86.31 |
| 4d | 9.91 | 90.82 |

Example 5: Chloroquine Loading Using Adenine and Aniline

During the development of embodiments of the technology provided herein, experiments were conducted to test liposome loading with other weak bases, e.g., adenine and aniline. The data collected indicated that loading liposomes according to the technology provided is not limited to the use of the weak base pyridine or its derivatives.

TABLE 6

Chloroquine loading with 0.5M adenine triflate

| | |
|---|---|
| lipid composition | DPPC:cholesterol 2:1 |
| loading base solution | 0.5M adenine triflate (0.5M with respect to adenine, supersaturated). |
| loading medium | 220 mM tris chloride buffer, pH 8.3 |
| base content prior to drug loading | 27.55 µmol per 80 µmol DPPC |
| µmol chloroquine added | 24 |
| percent of chloroquine loaded | 74.76 |

Adenine is a weak base (pKa 4.15) that has very limited solubility in water. Unlike pyridine, 2-methoxypyridine, and pyridazine, adenine is a solid at room temperature. The solubility of adenine is greatly increased when converted to a salt of a strong acid, e.g., triflic acid. In the experiments described herein, adenine triflate was supersaturated by warming to 75° C. immediately prior to use.

TABLE 7

| Chloroquine loading using 1.5M aniline triflate | |
| --- | --- |
| lipid composition | DPPC:cholesterol 2:1 |
| loading base solution | 1.5M aniline triflate (1.5M with respect to aniline) |
| loading medium | 220 mM tris chloride buffer, pH 8.3 |
| base content prior to drug loading | 20.66 μmol per 80 μmol DPPC |
| μmol chloroquine added | 24 |
| percent of chloroquine loaded | 54.36 |

Aniline is a weak base (pKa 4.19). Aniline is a hydrophobic liquid with limited solubility in water. Aniline forms salts with strong acids such as triflic acid. Experiments were conducted using the salt aniline triflate to load chloroquine into liposomes and subsequently monitor the leakage of chloroquine from the liposomes following loading.

Figure 10:
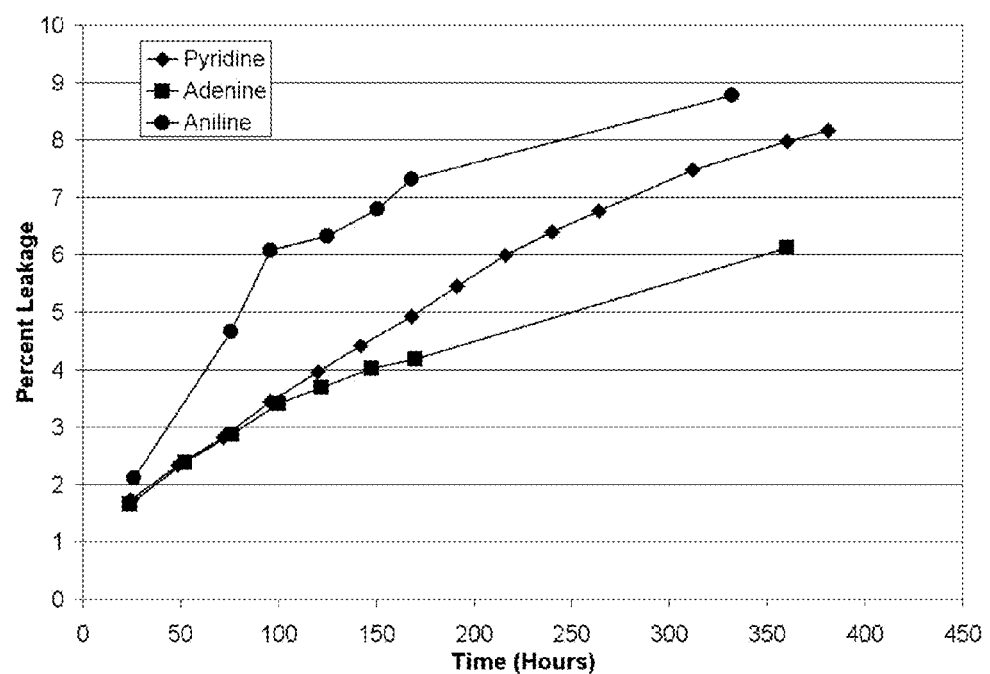
FIG. 10 is a plot showing leakage of chloroquine from liposomes loaded with adenine triflate (squares), aniline triflate (circles), or pyridine sulfate (diamonds).

Data were collected comparing the leakage of chloroquine from liposomes loaded using adenine triflate or aniline triflate with leakage of chloroquine from liposomes loaded using pyridinium sulfate (FIG. 10). For all three loading bases, the data indicated that leakage begins with a very small initial release of around 2% of the captured drug, rising to 6-9% over 350 hours (FIG. 10). Leakage is quite comparable for all three loading bases, though leakage is most rapid for aniline and least rapid for adenine Therefore, the data indicate that these three different weak bases having similar pKa values though quite different physical properties produce chloroquine loaded liposomes with similar leakage characteristics.

Example 6: Doxycycline Loading with 2-Methoxypyridinium Sulfate

Doxycycline is an antibacterial drug whose therapeutic use would greatly improve if incorporated into a controlled release formulation. For example, doxycycline has been loaded into liposomes using acid loading techniques (see, e.g., U.S. patent application Ser. No. 14/030,131, incorporated herein by reference). During the development of embodiments of the technology provided herein, experiments were conducted to incorporate doxycycline into liposomes using 2-methoxypyridinium sulfate. Data collected indicated that doxycycline loaded into liposomes using a weak base had a remarkably slow release profile for the drug.

TABLE 8

| Doxycycline loading using 2-methoxypyridinium sulfate | |
| --- | --- |
| lipid composition | DPPC:cholesterol 2:1 |
| loading base solution | 1.0M 2-methoxypyridinium sulfate (2M with respect to 2-methoxypyridine) |
| loading medium | 200 mM sodium citrate buffer, pH 3.5 |
| base content prior to drug loading | 17.09 μmol per 80 μmol DPPC |
| μmol doxycycline added | 16 |
| percent of doxycycline loaded | 87.03 |

Figure 11:
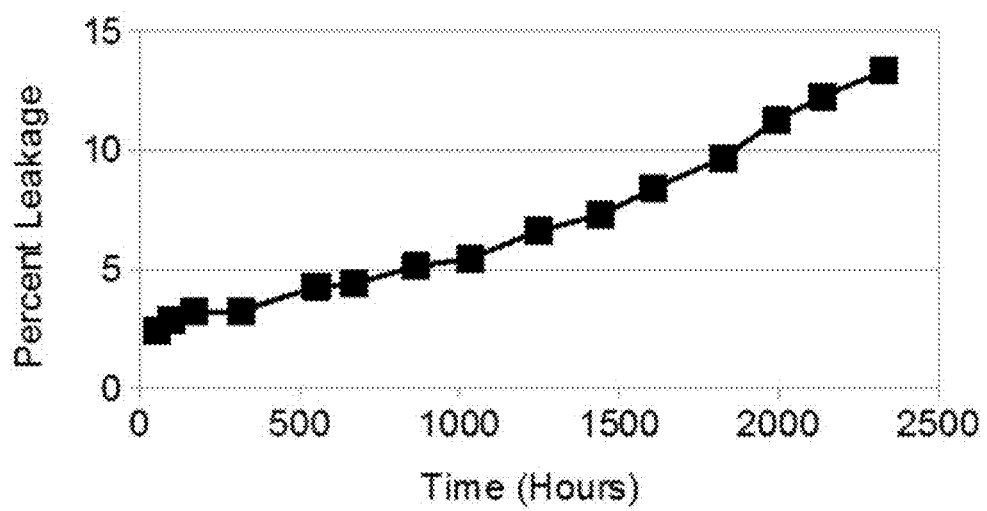
FIG. 11 is a plot showing leakage of doxycycline from liposomes loaded with 2-methoxypyridinium sulfate.

The initial leakage of doxycyline was low, e.g., approximately 2%, and the subsequent release rate was extremely low, e.g., only 13.34% released in 2300 hours. See, e.g., FIG. 11. This is an improved (e.g., lower) rate of release for doxycycline from liposomes relative to present technologies (see, e.g., Franklin (2015), Drug Metab Dispos 43: 1236-45).

Example 7: Buprenorphine Loading Using Acids

Buprenorphine and other drugs have been efficiently loaded into liposomes using acid loading techniques (see, e.g., U.S. patent application Ser. No. 14/030,131, incorporated herein by reference). For example, methods comprise preparing liposomes in a solution of acid (e.g., sulfuric acid), adding the drug, and neutralizing the external acid solution. In addition, experiments conducted during the development of embodiments of the technology provided herein indicated that other acids, e.g., hydrochloric acid and eprodisic acid, provide efficient loading. Furthermore, the data collected from experiments using eprodisic acid indicated that eprodisic acid provided an improved (e.g., slow) early phase of leakage, similar to that achieved with salts of weak bases.

TABLE 9

| Buprenorphine loaded using 1M hydrochloric acid | |
| --- | --- |
| lipid composition | DPPC:cholesterol 2:1 |
| loading solution | 1.0M hydrochloric acid |
| loading medium | 200 mM sodium acetate buffer, pH 3.5, adjusted with NaOH |
| μmol buprenorphine added | 9 |
| percent of buprenorphine loaded | 68.65 |

TABLE 10

| Buprenorphine loaded using 0.5M eprodisic acid | |
| --- | --- |
| lipid composition | DPPC:cholesterol 2:1 |
| loading solution | 0.5M eprodisic acid |
| loading medium | 200 mM sodium citrate buffer, pH 3.5, adjusted with NaOH |
| base content prior to drug loading | 20.66 μmol per 80 μmol DPPC |
| μmol buprenorphine added | 9 |
| percent of buprenorphine loaded | 73.39 |

Leakage of buprenorphine from liposomes following acid loading was rapid when the acid used for loading was hydrochloric acid. However, release was very limited when the loading acid was eprodisic acid (see, e.g., FIG. 12). Hence, use of eprodisic acid provides an improved acid loading technology. Accordingly, embodiments of the technology comprise use of eprodisic acid and eprodisate salts to improve the release characteristics of drugs loaded into liposomes.

Example 8: Chloroquine Loading Using Salts of Eprodisic Acid

During the development of embodiments of the technology provided herein, experiments were conducted to test the loading of chloroquine into liposomes using salts of eprodisic acid. In particular, chloroquine was loaded into liposomes using 0.5 M 2-methoxpyridinium eprodisane and 0.5 M pyridinium eprodisate.

TABLE 11

Chloroquine loaded using 0.5M 2-methoxypyridinium eprodisate

| | |
|---|---|
| lipid composition | DPPC:cholesterol 2:1 |
| loading base solution | 0.5M 2-methoxypyridinium eprodisate. (1.0M with respect to 2-methoxypyridine) |
| loading medium | 200 mM sodium citrate buffer, pH 3.5 |
| base content prior to drug loading | 26.19 μmol per 80 μmol DPPC. |
| μmol chloroquine added | 24 |
| percent of chloroquine loaded | 74.71 |

TABLE 12

Chloroquine loaded using 0.5M pyridinium eprodisate

| | |
|---|---|
| lipid composition | DPPC:cholesterol 2:1 |
| loading base solution | 0.5M pyridinium eprodisate. (1.0M with respect to pyridine) |
| loading medium | 220 mM tris chloride buffer, pH 8.3 |
| base content prior to drug loading | 41.96 μmol per 80 μmol DPPC |
| μmol chloroquine added | 24 |
| percent of chloroquine loaded | 85.71 |

Figure 12:
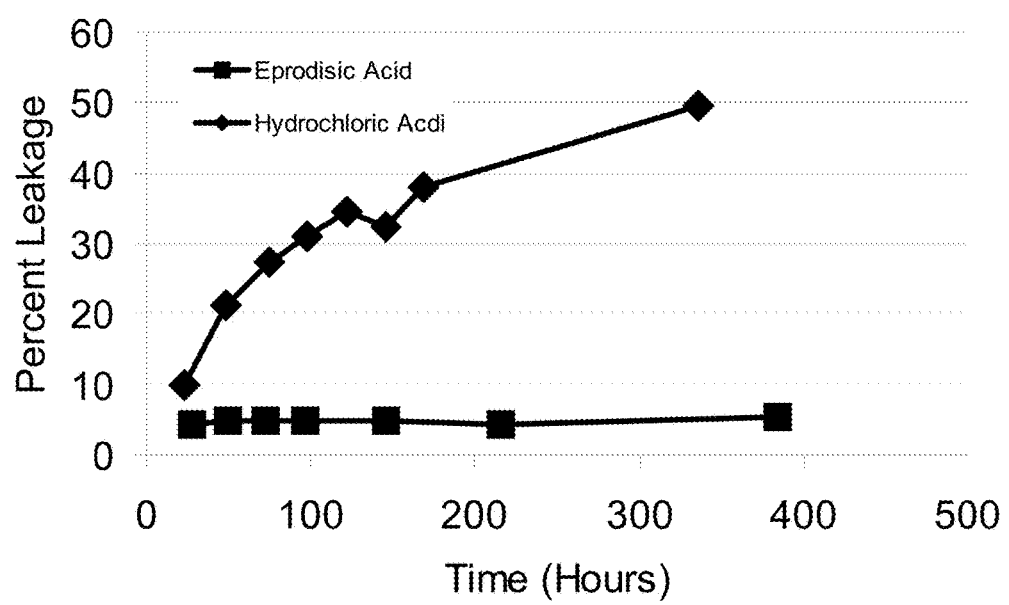
FIG. 12 is a plot showing leakage of buprenorphine from liposomes loaded with hydrochloric acid (diamonds) and eprodisic acid (squares).
Figure 13:
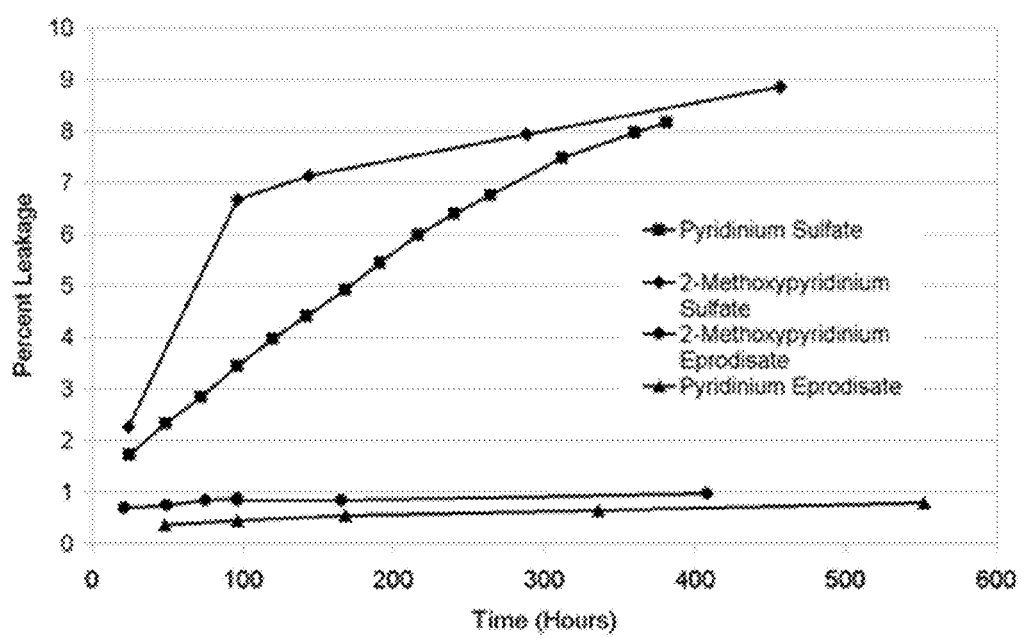
FIG. 13 is a plot showing release of chloroquine from DPPC:cholesterol liposomes loaded using 0.5 M pyridinium eprodisate (triangles) or 0.5 M 2-methoxypyridinium eprodisate (circles) compared to pyridinium sulfate (squares) and 2-methoxypyridinium sulfate (diamonds).

Buprenorphine loaded with eprodisic acid is released more slowly compared to buprenorphine loaded with hydrochloric acid or sulfuric acid (see, e.g., FIG. 12). The leakage of drugs loaded with a weak base sulfate salt or a weak base chloride salt is lower than is seen for sulfuric acid loaded drugs. Moreover, leakage is further reduced by using an eprodisate salt for loading. For example, the data collected during the development of embodiments of the technology indicated slower leakage for chloroquine loaded into liposomes with either 2-methoxypyridinium eprodisate or pyridinium eprodisate relative to the leakage of chloroquine loaded into liposomes using 0.5 M pyridinium sulfate or 0.5 M 2-methoxypyridinium sulfate (FIG. 13). While leakage of chloroquine loaded with a sulfate salt of pyridine is 4-8% after 400 hours, leakage of chloroquine loaded with the eprodisate salts of both pyridine and 2-methoxypyridine is only 1% or less after 400 hours. Therefore, eprodisate salts provide an improved salt for loading liposomes relative to sulfate or chloride salts for drug release.

Example 9: Loading Using 0.2 M Nicotinamide Sulfate

Nicotinamide is a weak base, pKa 3.25, which, structurally, is a pyridine. Unlike pyridine, 2-methoxypyridine, and pyridazine, it is a solid at room temperature. The solubility of nicotinamide is greatly increased when converted to a salt of a strong acid, giving solutions as concentrated as 4M at pH 2-3 and room temperature with most strong acids. Nicotinamide is a highly desirable choice for drug loading, because it is the amide of Vitamin B3, nicotinic acid. Therefore, there are no issues associated with administration of materials that may contain it to human or animal subjects. Nicotinamide may be administered orally at doses as high as 3 gm/day with no toxic effects.

TABLE 13

Doxycycline loading using 0.2M Nicotinamide Sulfate

| | |
|---|---|
| Lipid Composition | DPPC:cholesterol 2:1 |
| Loading Base Solution | 0.2M nicotinamide sulfate (0.4M with respect to nicotinamide). |
| Loading medium | 200 mM sodium citrate buffer, pH 3.5. |
| Base Content Prior to Drug Loading | 83.13 μmol per 80 μmol Phospholipon 90H |
| μmol Doxycycline Added | 74.82 |
| Percent of Doxycycline Loaded | 69.5 |

The pKa of nicotinamide is comparable to that of 2-methoxypyridine, making it a suitable base to use for loading at the low pH required for working with buprenorphine and doxycycline. Table 13 shows that doxycycline can be loaded efficiently at pH 3.5 using nicotinamide sulfate.

TABLE 14

Naltrexone Loading using 0.2M Nicotinamide Sulfate.

| | |
|---|---|
| Lipid Composition | DPPC:cholesterol 2:1 |
| Loading Base Solution | 0.2M nicotinamide sulfate (0.4M with respect to nicotinamide). |
| Loading medium | 220 mM sodium citrate buffer, pH 7.0. |
| Base Content Prior to Drug Loading | 33.18 μmol per 26 μmol Phospholipon 90H |
| μmol Naltrexone Added | 29.86 |
| Percent of Naltrexone Loaded | 86.28 |

Nicotinamide sulfate was also used to load naltrexone into liposomes successfully, as shown in table 14. Naltrexone loading may be done at higher pH values than loading of doxycycline, and this is reflected in the higher efficiency of loading for naltrexone.

Example 10: In Vivo Administration of Buprenorphine in Liposomes

During the development of embodiments of the technology provided herein, buprenorphine was loaded into liposomes using sulfate or eprodisate salts (see Tables 15-18) and administered to rats to measure serum concentrations of buprenorphine as a function of time for the liposome preparations. Serum buprenorphine concentrations were monitored following a single 2 mg/Kg injection of buprenorphine loaded in liposomes.

TABLE 15

Buprenorphine Loaded into DPPC liposomes using 0.24M 2-methoxypyridinium sulfate

| | |
|---|---|
| lipid composition | DPPC:cholesterol 2:1 |
| loading base solution | 0.24M 2-methoxypyridinium sulfate. (0.48M with respect to 2-methoxypyridine) |
| loading medium | 200 mM sodium citrate buffer, pH 3.5 |
| base content prior to drug loading | 6.13 μmol per 80 μmol DPPC |
| μmol buprenorphine added | 9 |
| percent of buprenorphine loaded | 49.78 |

TABLE 16

Buprenorphine loaded into DSPC liposomes using 0.24M 2-methoxypyridinium sulfate

| | |
|---|---|
| lipid composition | DSPC:cholesterol 2:1 |
| loading base solution | 0.24M 2-methoxypyridinium sulfate. (0.48M with respect to 2-methoxypyridine) |

TABLE 16-continued

Buprenorphine loaded into DSPC liposomes
using 0.24M 2-methoxypyridinium sulfate

| | |
|---|---|
| loading medium | 200 mM sodium citrate buffer, pH 3.5 |
| base content prior to drug loading | 14.43 μmol per 80 μmol DPPC |
| μmol buprenorphine added | 9 |
| percent of buprenorphine loaded | 83.41 |

TABLE 17

Buprenorphine loaded into DPPC liposomes using
0.24M 2-methoxypyridinium eprodisate

| | |
|---|---|
| lipid composition | DPPC:cholesterol 2:1 |
| loading base solution | 0.24M 2-methoxypyridinium eprodisate. (0.48M with respect to 2-methoxypyridine) |
| loading medium | 200 mM sodium citrate buffer, pH 3.5 |
| base content prior to drug loading | 6.28 μmol per 80 μmol DPPC |
| μmol buprenorphine added | 9 |
| percent of buprenorphine loaded | 67.58 |

TABLE 18

Buprenorphine loaded into DSPC liposomes using
0.24M 2-methoxypyridinium eprodisate

| | |
|---|---|
| lipid composition | DSPC:cholesterol 2:1 |
| loading base solution | 0.24M 2-methoxypyridinium eprodisate. (0.48M with respect to 2-methoxypyridine) |
| loading medium | 200 mM sodium citrate buffer, pH 3.5 |
| base content prior to drug loading | 23.76 μmol per 80 μmol DPPC |
| μmol buprenorphine added | 9 |
| percent of buprenorphine loaded | 81.93 |

Figure 14:
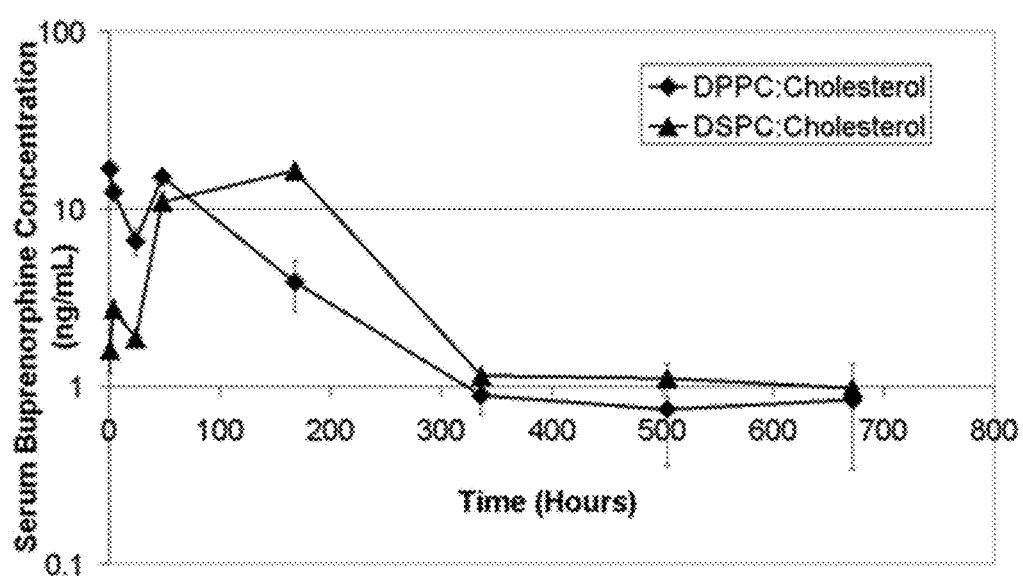
FIG. 14 is a plot showing serum buprenorphine concentrations following a single 2 mg/Kg injection of buprenorphine in DPPC:cholesterol (diamonds) or DSPC:cholesterol (triangles) liposomes loaded with 0.24 M 2-methoxypyridinium sulfate.

Data were collected from the administration of buprenorphine loaded into liposomes using sulfate salts. FIG. 14 shows the serum concentrations in rats following a single subcutaneous injection of 2 mg/Kg buprenorphine in liposomes. Two preparations were studied in this experiment, which are summarized in Table 15 and Table 16.

The serum concentration of buprenorphine loaded and administered in DPPC liposomes was approximately 20 ng/mL in the first 48 hours after administration (FIG. 14). After one week, the concentration declined to approximately 4 ng/mL and then plateaued at a value of 1 ng/mL at 2-4 weeks (FIG. 14).

The serum concentration of buprenorphine loaded and administered in DSPC liposomes was lower during the first 24 hours (approximately 2-3 ng/mL) and peaked at approximately 10-20 ng/mL at 48 hours to 1 week after administration (FIG. 14). Thereafter, the serum concentration plateaued at approximately 1 ng/mL (FIG. 14). Generally, liposomes prepared from DSPC are more stable than those prepared from DPPC and this is reflected in the lower concentrations at 4-24 hours and the later peak serum concentrations (FIG. 14).

Figure 15:
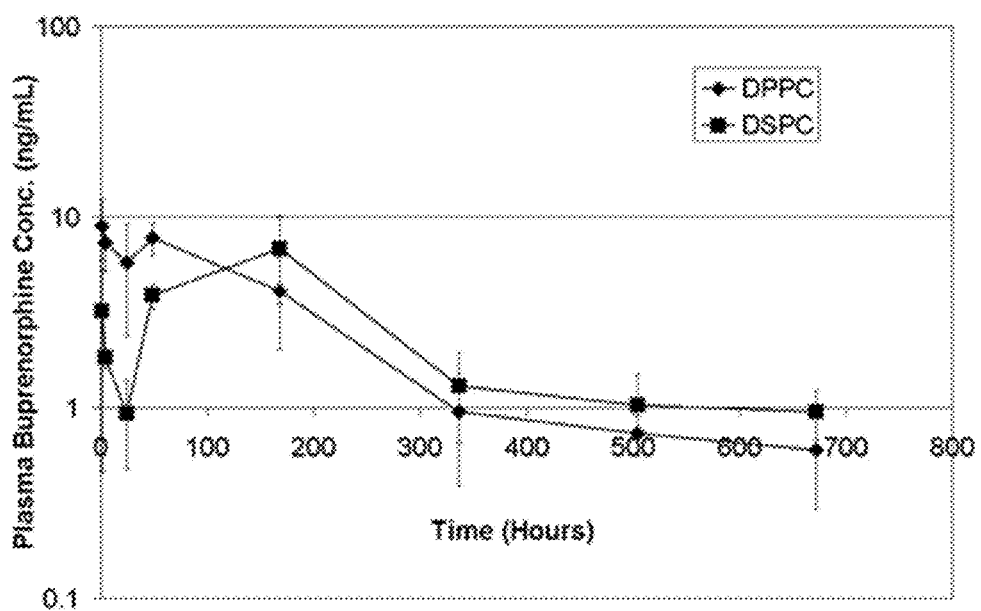
FIG. 15 is a plot showing serum buprenorphine concentrations following a single 2 mg/Kg injection of buprenorphine in DPPC:cholesterol (diamonds) or DSPC:cholesterol (squares) liposomes loaded with 0.24 M 2-methoxypyridinium eprodisate.

Data were collected from the administration of buprenorphine loaded into liposomes using eprodisate salts. FIG. 15 shows the serum concentrations in rats following a single injection of 2 mg/Kg buprenorphine in liposomes. Two preparations were studied in this experiment, which are summarized in Table 17 and Table 18.

The serum concentration of buprenorphine loaded and administered in DPPC liposomes was approximately 6 ng/mL in the first 48 hours. After one week, the concentration declined to approximately 4 ng/mL and then plateaued at a value of 0.6 ng/mL at 2-4 weeks.

The serum concentration of buprenorphine loaded and administered in DSPC liposomes was lower during the first 24 hours (e.g., approximately 2-3 ng/mL) and peaked at approximately 6 ng/mL at 1 week. Thereafter, plateau concentrations of approximately 1 ng/mL were detected.

Accordingly, these data indicate that the peak serum concentrations of buprenorphine administered in liposomes loaded with 2-methoxypyridinium eprodisate (which occur during the first week) are approximately 40% of the peak serum concentrations of buprenorphine detected when buprenorphine is administered in liposomes loaded with 2-methoxypyridinium sulfate salt. This is consistent with the observed lower release rate seen for eprodisate-loaded drugs. The difference between DPPC and DSPC is very similar for the two salts. The data indicated a long-term maintenance of therapeutically significant buprenorphine serum concentrations in rats, paralleling the low in vitro release rates of buprenorphine from liposomes prepared and loaded according to the technology provided herein. In conclusion, eprodisate appears to be beneficial in providing serum concentrations that are more constant over time following injection.

Example 11: Liposome Preparation by Solvent Dilution

In some embodiments, liposomes are prepared by suspending a phospholipid:cholesterol mixture in chloroform, removing the chloroform, resuspending the lipid in t-butanol, freeze-drying the solution, and then suspending the lipid lyophilizate in a solution containing either an acid or a salt. However, most phospholipids and cholesterol are provided by commercial suppliers as solids. Accordingly, provided herein are embodiments of a method of liposome preparation that eliminates several steps, including the use of chloroform, to provide a method with fewer steps.

For example, in some embodiments of the method, phospholipid is mixed with an alcohol to provide a solution of phospholipid in the alcohol. For example, during experiments conducted during the development of embodiments of the technology, 60 mg of a commercial phosphatidylcholine (PHOSPHOLIPON 90H, comprising at least 90% hydrogenated phosphatidylcholine) and 15 mg of cholesterol were mixed in a tube. Then, 100 microliters of 2-propanol were added to the lipid/cholesterol mixture. The mixture was warmed to 53 to 58° C., which provided a clear solution of lipids in the alcohol solvent.

Then, 0.25 mL (a first volume or an initial volume) of a weak base salt (e.g., pyridinium sulfate or 2-methoxypyridinium sulfate) warmed to the same temperature as the lipid in alcohol (e.g., 53 to 58° C.) was added to the solution of lipids in the alcohol warmed at 53 to 58° C. After adding the weak base salt, a viscous, turbid suspension of liposomes was formed. The mixture was mixed gently for 5 minutes, after which an additional 0.25 mL (a second volume) of the base salt was added with further mixing. The resultant suspension was cooled to room temperature, below the phase transition temperature of the phospholipid, and then diluted with 0.9% w/v NaCl (saline) to 13 mL. The suspension was sedimented and washed to eliminate unincorporated base, and the base content of the liposomes was then measured spectroscopically according to procedures described above.

TABLE 19

Incorporation of base salts into liposomes using solvent dilution

| base salt concentration | base salt | base content (mol/mol) hydration of lyophilized lipid | solvent dilution |
|---|---|---|---|
| 0.25M | pyridinium sulfate | ND | 0.94 |
| 0.5M | | 0.334 | 1.32 |
| 1.0M | | 0.756 | 2.54 |
| 1.5M | | 1.8 | 3.16 |
| 0.25M | 2-methoxypyridinium sulfate | 0.075 ± 0.002 | 0.35 |
| 0.5M | | 0.158 ± 0.044 | 0.58 |
| 1.0M | | 0.885 ± 0.612 | 1.81 |
| 0.2M | pyridinium eprodisate | ND | 0.93 |
| 0.2M | 2-methoxypyridinium eprodisate | ND | 0.32 |
| 0.25M | | 0.079 | 0.49 |

Table 19 shows the amount of either pyridine or 2-methoxypyridine incorporated into liposomes using the solvent dilution technology described herein (Table 19, "solvent dilution"). Data collected for incorporation of pyridine and 2-methoxypyridine into liposomes using traditional chloroform dissolution, drying, and hydration are given for comparison (Table 19, "hydration of lyophilized lipid"). The data collected indicate that the base content for liposomes prepared by hydration rises steeply as the base salt concentration is increased. Without being bound by theory, it is contemplated that this relationship reflects an increase in the capture volume of the liposomes, possibly caused by solvation effects of these two bases. In contrast, two-step solvent dilution as described herein provides base incorporation that is proportional to the salt concentration. Furthermore, base incorporation produced by the technology described herein is more efficient than base incorporation provided by hydration. Base capture was much greater for a given base salt concentration, and the efficiency is effectively doubled by use of smaller base salt volumes (e.g., 1 mL was used to hydrate lipids in the traditional method and 0.5 mL was used to prepare liposomes in the solvent dilution method). In addition, the solvent dilution technology described herein is highly controllable and is amenable to scale-up, e.g., including but not limited to production of liposomes comprising sulfate salts and eprodisate salts of both pyridine and 2-methoxypyridine.

Example 12: Volume Ratios for Alcohol Dilution

As described above, embodiments of the solvent dilution method involve the two-step addition of an aqueous solution to a lipid mixture in alcohol. In the particular experimental preparations described above, the first and second volumes added were each 250 microliters. During the development of embodiments of the technology, experiments were conducted to test capture of weak base salt in liposomes as a function of the two volumes of base salt added to the preparation. In particular, liposomes were prepared by dissolving 60 mg of a commercial phosphatidylcholine (PHOSPHOLIPON 90H, comprising at least 90% hydrogenated phosphatidylcholine) and 15 mg cholesterol in 100 microliters of 2-propanol at 58° C. Then, a "first volume" of pyridinium sulfate or 2-methoxypyridinium sulfate (2-MP) was added and the solution was warmed at 58° C. for 5 minutes (Table 20). Next, a "second volume" of pyridinium sulfate or 2-methoxypyridinium sulfate was added (Table 20) and the mixture was cooled to room temperature and diluted in 0.99% w/v NaCl.

TABLE 20

Encapsulation efficiency of 0.2M pyridinium sulfate and 0.2M 2-methoxypyridinium sulfate as a function of volume of base salt added to lipid in 2-propanol

| First Volume (microliter) | Second Volume (microliter) | Pyridine Capture (mol/mol) | Pyridine Capture Efficiency (%) | 2-MP Capture (mol/mol) | 2-MP Capture Efficiency (%) |
|---|---|---|---|---|---|
| 150 | 350 | 0.537 | 21.48 | 0.067 | 2.68 |
| 200 | 300 | 0.511 | 20.44 | 0.116 | 4.64 |
| 250 | 250 | 0.718 | 28.72 | 0.265 | 10.6 |
| 300 | 200 | ND | | 0.258 | 10.32 |
| 350 | 150 | 1.057 | 42.28 | 0.433 | 17.32 |
| 400 | 100 | 1.136 | 45.44 | 0.185 | 7.4 |
| 450 | 50 | 1.012 | 40.48 | ND | — |
| 500 | 0 | 0.860 | 34.4 | ND | — |

Data were collected during the experiments from measurements of the encapsulation efficiency of 0.2 M pyridinium sulfate or 0.2 M 2-methoxypyridinium sulfate as a function of the initial volume of base salt added (Table 20). The data indicated that the most efficient capture of 2-methoxypyridine occurs when the lipid suspended in 100 microliters of 2-propanol is diluted first with 350 microliters of loading base, held at 58° C. for 5 minutes, and then diluted with a further 150 microliter of loading base solution before cooling and diluting with saline (Table 20). For pyridinium salts, the data indicated that the highest capture occurs by adding 400 microliters of loading base, incubating at 58° C. for 5 minutes, then adding 100 microliters of loading base before cooling and diluting with saline (Table 20). These data indicate that the method provides a high efficiency of capture. For example, the best observed loading of pyridine by this method was an incorporation efficiency of approximately 45% of the added pyridinium salt being incorporated into the liposomes. Efficiency of capture of 2-methoxypyridine is lower.

Example 13: Choice of Alcohol for Alcohol Dilution Method

During the development of embodiments of the technology described herein, similar experiments were conducted to measure the capture of 0.2 M pyridinium and 2-methoxypyridinium sulfate in liposomes using t-butanol (Table 21). As before, the lipid was suspended in 100 microliters of the alcohol (t-butanol) at 62° C. and the first volume of base salt was added. After 5 minutes at 62° C., the second volume of base salt was added, the mixture was cooled and washed with saline before measuring the incorporated base content.

TABLE 21

Encapsulation efficiency of 0.2M pyridinium sulfate and 0.2M 2-methoxypyridinium sulfate as a function of the volume of base salt added to lipid in t-butanol.

| First Volume (microliter) | Second Volume (microliter) | Pyridine Capture (mol/mol) | Pyridine Capture Efficiency (%) | 2-MP Capture (mol/mol) | 2-MP Capture Efficiency (%) |
|---|---|---|---|---|---|
| 200 | 300 | ND | — | 0.118 | 4.72 |
| 250 | 250 | 0.87 | 34.8 | ND | — |
| 300 | 200 | ND | — | 0.147 | 5.88 |
| 400 | 100 | ND | — | 0.207 | 8.28 |
| 500 | 0 | 0.93 | 37.2 | 0.290 | 11.6 |
| 600 | 0 | 0.95 | 31.66 | 0.373 | 12.43 |
| 700 | 0 | 0.84 | 24.0 | 0.239 | 6.83 |

TABLE 21-continued

Encapsulation efficiency of 0.2M pyridinium sulfate and 0.2M 2-methoxypyridinium sulfate as a function of the volume of base salt added to lipid in t-butanol.

| First Volume (microliter) | Second Volume (microliter) | Pyridine Capture (mol/ mol) | Pyridine Capture Efficiency (%) | 2-MP Capture (mol/ mol) | 2-MP Capture Efficiency (%) |
|---|---|---|---|---|---|
| 800 | 0 | 1.97 | 49.25 | ND | — |
| 1000 | 0 | 0.13 | 2.6 | ND | — |
| 1200 | 0 | 0.20 | 3.33 | ND | — |
| 1400 | 0 | 0.17 | 2.43 | ND | — |

The data collected indicated that a higher initial volume of base salt is required for efficient loading using lipids dissolved in t-butanol (Table 21) than the volume of base salt required for efficient loading using lipids dissolved in 2-propanol (Table 20). Despite this, the efficiency of loading of pyridinium sulfate with t-butanol is significantly higher than for 2-propanol at the ratios providing the highest loading efficiencies. Loading efficiency, however, is lower with t-butanol than with 2-propanol for 2-methoxypyridinium sulfate. During the development of the embodiments described herein, experiments were also conducted to compare the efficacy of t-butanol and 2-propanol to ethanol and methanol. In particular, liposomes were prepared by dissolving 60 mg of a commercial phosphatidylcholine (PHOSPHOLIPON 90H, comprising at least 90% hydrogenated phosphatidylcholine) and 15 mg cholesterol in 100 microliters of each alcohol tested at the preparation temperature indicated (Table 22).

TABLE 22

Capture efficiency of 0.2M pyridinium sulfate or 0.2M 2-methoxypyridinium sulfate as a function of alcohol

| Alcohol | number of carbons | preparation temperature (° C.) | pyridine capture (mol/mol phospholipid) | 2-MP capture (mol/mol phospholipid) |
|---|---|---|---|---|
| Methanol | 1 | 59 | 0.0595 | 0.007 |
| Ethanol | 2 | 60 | 0.238 | 0.0015 |
| 2-propanol | 3 | 59 | 0.718 | 0.283 |
| t-butanol | 4 | 62 | 0.869 | 0.161 |

Then, 250 microliters of prewarmed 0.2 M pyridinium sulfate or 2-methoxypyridinium sulfate (2-MP) were added to the dissolved lipid in alcohol and the mixture was incubated at the preparation temperature for 5 minutes. Next, an additional 250 microliters of prewarmed 0.2 M pyridinium sulfate or 2-methoxypyridinium sulfate was then added and the mixture was cooled to room temperature. The liposomes were then diluted with 0.99% w/v NaCl and non-encapsulated pyridine was removed by three sedimentations in a bench top centrifuge at 1600×g for 5 minutes. Pyridine content in the resuspended final pellet was measured spectroscopically. The data collected during the experiments indicated that 2-propanol and t-butanol provided incorporation of weak base into liposomes by the solvent dilution method that was better than incorporation of weak base into liposomes by the solvent dilution using methanol or ethanol (Table 22).

In addition, experiments were conducted during the development of embodiments of the technology to test the use of 1-propanol (Table 23), 2-butanol (Table 24), and 1-butanol (Table 25). In particular, Table 23 shows the loading of 2-methoxypyridinium sulfate and pyridinium sulfate using 1-propanol as the alcohol for lipid dissolution, Table 24 shows the loading of 2-methoxypyridinium sulfate and pyridinium sulfate using 2-butanol as the alcohol for lipid dissolution, and Table 25 shows the loading of pyridinium sulfate using 1-butanol.

The data collected during the experiments indicated that 1-propanol (Table 23) was more effective in some embodiments of the technology than 2-propanol and t-butanol (compare Table 23 with Tables 20 and 21) with respect to the amount and the percentage of pyridine incorporated into the liposomes. In addition, the data indicated that high loading efficiencies were provided by preparing liposomes by adding 500-600 microliters of the aqueous phase to the lipid solution in the alcohol for pyridinium sulfate and adding 700 microliters of the aqueous phase to the lipid solution in the alcohol for 2-methoxypyridinium sulfate (Table 23). These volumes are greater for 1-propanol than for 2-propanol. Given that 1-propanol has a log P of 0.329 and 2-propanol has a log P of 0.16, some embodiments of the methods using 1-propanol may require more dilution to achieve the desired alcohol concentration in the lipid for optimal liposome formation and solute capture.

TABLE 23

Capture of pyridinium and 2-methoxypyridinium salts by alcohol dilution using 1-propanol

| First Volume (microliter) | Second Volume (microliter) | Pyridine Capture (mol/ mol) | Pyridine Capture Effiency (%) | 2-MP Capture (mol/ mol) | 2-MP Capture Efficiency (%) |
|---|---|---|---|---|---|
| 100 | 400 | 1.71 | 68.48 | ND | — |
| 200 | 300 | 1.41 | 56.45 | 0.21 | 7.64 |
| 300 | 200 | 1.16 | 46.25 | 0.17 | 6.33 |
| 400 | 100 | 1.05 | 41.87 | 0.17 | 6.24 |
| 500 | 0 | 1.72 | 68.93 | 0.39 | 13.76 |
| 600 | 0 | 1.93 | 64.45 | 0.47 | 13.65 |
| 700 | 0 | 1.59 | 45.51 | 0.96 | 24.11 |
| 800 | 0 | ND | — | 0.56 | 12.33 |

Although 2-butanol is not miscible with water in all ratios, it has significant solubility in aqueous solutions. In particular, 2-butanol has an aqueous solubility of 290 g/L and a density of 0.808 g/mL. Accordingly, 2-butanol mixes freely with aqueous solutions when an aqueous volume of at least 0.2-0.3 mL is added to 0.1 mL 2-butanol. In the case of pyridinium salts, 2-butanol (Table 24) provides higher loading efficiencies than 2-propanol (Table 18), both in terms of the amount and the percentage of pyridine incorporated into the liposomes. Further, 2-butanol provides higher loading than 1-propanol (Table 23) in terms of the amount of salt captured, though not in terms of maximum capture efficiency. For the volumes that produce the most efficient loading, the volume of aqueous phase added to the lipid solution in the alcohol is greater for 2-butanol than it is for either 1-propanol or 2-propanol. Given that 2-butanol has a log P of 0.683, 1-propanol has a log P of 0.329, and 2-propanol has a log P of 0.16, some embodiments of the methods using 2-butanol may require more dilution to achieve the desired alcohol concentration in the lipid for optimal liposome formation and solute capture.

TABLE 24

Capture of pyridinium and 2-methoxypyridinium
salts by alcohol dilution using 2-butanol

| First Volume (microliter) | Second Volume (microliter) | Pyridine Capture (mol/mol) | Pyridine Capture Efficiency (%) | 2-MP Capture (mol/mol) | 2-MP Capture Efficiency (%) |
|---|---|---|---|---|---|
| 200 | 400 | 0.43 | 17.35 | ND | |
| 300 | 300 | 0.49 | 19.52 | ND | |
| 400 | 200 | 0.52 | 20.62 | ND | |
| 500 | 100 | 0.39 | 15.58 | ND | |
| 600 | 0 | 0.94 | 31.39 | ND | |
| 700 | 0 | 1.44 | 41.19 | ND | |
| 800 | 0 | 2.26 | 56.60 | 0.37 | 9.31 |
| 900 | 0 | 2.69 | 59.68 | ND | |
| 1000 | 0 | 3.06 | 61.24 | 0.54 | 10.77 |
| 1100 | 0 | 2.94 | 53.41 | ND | |
| 1200 | 0 | 2.62 | 43.70 | 0.34 | 5.64 |

1-butanol is also not fuly miscible with water, and has a solubility of 72 g/L. An optimization study for the capture of 0.2 M pyridinium sulfate in liposomes using 1-butanol is shown in table 25. As before, the lipid was suspended in 100 microliter of the alcohol, t-butanol, at 60° C., and the base salt was added. After 5 minutes at 60° C., the mixture was then cooled and washed with saline before measuring the base content. 1-butanol requires addition of greater volumes of base salt for liposome formation. This is believed to be required because 1-butanol is a more hydrophobic alcohol with less water solubility than either 2-butanol or 1-propanol. Efficiency of encapsulation appears to be less than is achieved with 1-propanol or 2-butanol, yet this alcohol might still find use in certain circumstances.

TABLE 25

Encapsulation efficiency of 0.2M pyridinium sulfate as a function
of the volume of base salt added to lipid in 1-butanol.

| Volume (microliter) | Pyridine Capture (mol/mol) | Pyridine Capture Efficiency (%) |
|---|---|---|
| 600 | 0.748 | 24.94 |
| 800 | 0.914 | 22.86 |
| 1000 | 1.057 | 21.14 |
| 1200 | 1.613 | 26.88 |
| 1400 | 1.457 | 20.82 |
| 1600 | 2.093 | 26.47 |
| 1800 | 1.565 | 17.39 |
| 2000 | 1.629 | 16.29 |

Methanol, ethanol, 1-propanol, 2-propanol, and t-butanol are five alcohols that are miscible with aqueous solutions; and, while 2-butanol, 1-butanol, and isobutanol are not fully miscible in aqueous solutions, these alcohols have significant aqueous solubility. Accordingly, the efficacy of 2-butanol and 1-butanol (above) for the preparation of liposomes indicates that the technology encompasses the use of alcohols with solubility of at least 50 g/liter, preferably 150 g/liter (e.g., alcohols with 1-6 carbon atoms, preferably 2-4 carbon atoms) in various embodiments of the technology to provide efficient liposome loading.

Example 14: Capture of Other Solutes Using Solvent Dilution

During the development of embodiments of the technology, experiments were conducted to measure the capture of the drugs doxycycline and chloroquine into liposomes using the solvent dilution methods described herein. The data collected indicated that the solvent (e.g., alcohol) dilution method is generally applicable, e.g., to a wide range of solutes and not limited to salts of hydrophobic liquids.

Doxycycline hyclate was dissolved in water at 8.25 mg/mL and captured using 2-propanol dilution. In particular, 60 mg of a commercial phosphatidylcholine (PHOSPHOLIPON 90H, comprising at least 90% hydrogenated phosphatidylcholine) and 15 mg cholesterol were dissolved in 100 microliters of 2-propanol at 58° C. Then, the initial volume of the doxycycline solution (pre-warmed to 58° C.) was added to the dissolved lipid (Table 23). After a 5-minute incubation at 58° C., the second volume of the doxycycline solution (pre-warmed to 58° C.) was added and the mixture was cooled to room temperature, washed with saline, and the incorporation efficiency was measured (Table 26).

TABLE 26

Doxycycline direct capture using 2-propanol dilution

| initial volume (microliter) | second volume (microliter) | doxycyline capture efficiency (%) | doxycycline capture (mol/mol phospholipid) |
|---|---|---|---|
| 200 | 300 | 33.108 | 0.033 |
| 250 | 250 | 26.322 | 0.026 |
| 300 | 200 | 30.527 | 0.031 |
| 350 | 150 | 25.845 | 0.026 |

Efficient capture for this drug appears less dependent on the initial volume ratio. The highest efficiency of incorporation achieved was about 33% and occurred when the initial volume of doxycycline solution was 200 microliters.

Chloroquine diphosphate was dissolved in 150 mM citrate buffer (pH 4.0) at a concentration of 200 mM and captured using 1-propanol dilution. Using the methods described above, 60 mg Phospholipon 90H and 15 mg cholesterol were dissolved in 100 microliters 1-propanol at 58° C. Then, the first volume of chloroquine solution (prewarmed to 58° C.) was added to the dissolved lipid solution. The mixture was incubated for 5 minutes at 58° C.; then, the second volume of chloroquine solution (prewarmed to 58° C.) was added and the mixture was cooled to room temperature. The capture results are shown in table 27.

TABLE 27

Chloroquine direct capture using 1-propanol dilution

| initial volume (microliter) | second volume (microliter) | chloroquine capture efficiency (%) | chloroquine capture (mol/mol phospholipid) |
|---|---|---|---|
| 300 | 200 | 29.82 | 0.373 |
| 400 | 100 | 39.70 | 0.496 |
| 500 | 0 | 56.45 | 0.706 |
| 600 | 0 | 48.79 | 0.610 |

The data indicated that the most efficient capture of chloroquine was approximately 56% at an initial volume of 500 μl (Table 27). This is a higher efficiency than doxycycline capture using 2-propanol, which is consistent with the superior efficiency of 1-propanol for capture of pyridine and 2-methoxypyridine discussed herein.

Example 15: Control of Leakage Rate by Selection of Counterion

Data collected during the development of embodiments of the technology provided herein indicate that the use of weak base loading in conjunction with sulfate or eprodisate produces liposome preparations having extremely low release (leakage) rates. However, a minimized release rate may not be desirable in all circumstances. Accordingly, some embodiments provide a technology to tailor the release rate as appropriate for the desired application.

During the development of embodiments of the technology, experiments were conducted to test control of release as a function of the weak base salt used for loading. In particular, liposomes were prepared from a commercial phosphatidylcholine (PHOSPHOLIPON 90H, comprising at least 90% hydrogenated phosphatidylcholine) and cholesterol at a 2:1 molar ratio using 2-propanol dilution. In the experiments, pyridinium salts of sulfate, eprodisate, methanesulfonate, benzenesulfonate, chloride, and nitrate were compared (Table 28). All pyridinium salts used were 0.4 M with respect to pyridine; hence the sulfate and eprodisate salts were 0.2 M with respect to sulfate or eprodisate and 0.4 M with respect to the other salts.

A mass of 60 mg of phosphatidylcholine and 15 mg cholesterol were mixed with 100 microliters of 2-propanol at 58° C. to form a clear suspension. Then, 400 microliters of a pyridinium salt solution (prewarmed to 58° C.) were added to the lipid suspension. The mixture was kept at 58° C. for 5 minutes and then 100 microliters of the pyridinium salt solution were added. The mixture was cooled and diluted with 0.99% w/v sodium chloride. After dilution, unencapsulated pyridine was removed by sedimentation in a benchtop centrifuge at 300×g for 5 minutes. A total of three washes were performed. Naltrexone solution was then added in 150 mM citrate (pH 7.0) and the mixture was left to load for 48 hours. After loading, residual non-loaded naltrexone and released pyridine were removed by dilution with saline and sedimentation a total of three times. Naltrexone and pyridine content were measured spectroscopically. The samples were subsequently monitored for release of naltrexone using the sedimentation method. The results of loading for the six different salts are summarized in Table 28. Two trials were performed for each condition.

TABLE 28

Naltrexone loading using pyridinium salts

| pyridinium salt | pyridine content before loading (micromol) | | naltrexone added (mg) | | percent naltrexone loaded | |
|---|---|---|---|---|---|---|
| | Experiment | | | | | |
| | 1 | 2 | 1 | 2 | 1 | 2 |
| Sulfate | 58.19 | 64.02 | 19.77 | 21.75 | 86.1 | 88.5 |
| Eprodisate | 74.67 | 74.83 | 25.37 | 25.43 | 85.6 | 84.2 |
| Methanesulfonate | 60.97 | 74.26 | 20.81 | 25.34 | 89.0 | 89.3 |
| Benzenesulfonate | 73.76 | 65.39 | 25.17 | 22.32 | 87.92 | 89.45 |
| Chloride | 63.06 | 64.91 | 21.52 | 22.15 | 88.24 | 89.74 |
| Nitrate | 43.90 | 55.78 | 14.98 | 19.02 | 78.6 | 75.0 |

The data collected indicated that all pyridinium salts produced loading of naltrexone in excess of 75%, though nitrate was somewhat less efficient than the other salts, which all produced loading in excess of 85%.

Figure 16:
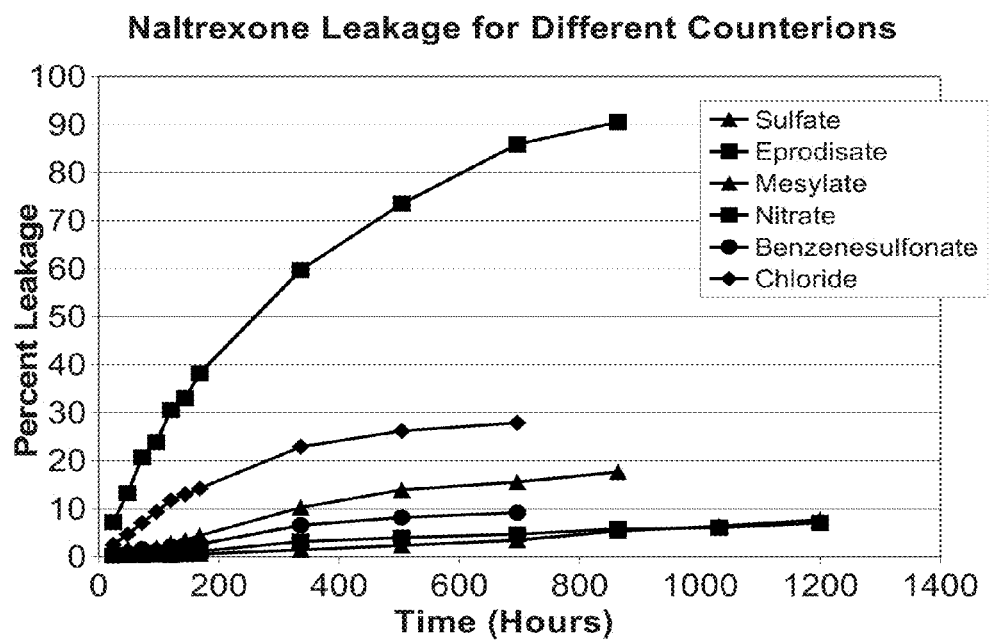
FIG. 16 is a plot showing the leakage of naltrexone from liposomes prepared with pyridinium salts of sulfate (filled triangles), eprodisate (filled squares), methane sulfonate ("mesylate", open triangles), benzenesulfonate (open circles), chloride (open diamonds), and nitrate (open squares).

In further experiments, data were collected with respect to the release of naltrexone from liposomes loaded with different pyridinium salts (FIG. 16). Loading with pyridinium sulfate and pyridinium eprodisate salts produced liposomes having a very low release rate, with only 5% or so release in 900 hours (FIG. 16). This is comparable to results obtained with buprenorphine and doxycycline. Benzenesulfonate and methanesulfonate salts produce liposomes having higher release rates. Without being bound by theory, this observation was expected because these are monobasic acids. The chloride salt gave a more rapid 20% release in about 300 hours; nitrate salt release was the fastest with over 70% release in 500 hours and 90% in 860 hours (FIG. 16). Release in all cases was uniform, with no evidence of an initial fast rate of release. These data indicate that the technology provided herein provides liposome formulations that release drug at a precisely determined and selected rate. Accordingly, the technology finds use in specific applications associated with a need to control the life time of a controlled release formulation.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the art are intended to be within the scope of the following claims.

We claim:

1. A method of producing liposomes comprising an encapsulant the method comprising:
   a) dissolving lipids in a solvent to produce a lipid solution, wherein said solvent is selected from the group consisting of a C3 and a C4 alcohol;
   b) adding an aqueous solution to the lipid solution to produce liposomes, wherein the aqueous solution comprises an encapsulant dissolved therein.

2. The method of claim 1, wherein the C3 alcohol is 1-propanol.

3. The method of claim 1, wherein the C4 alcohol is 2-butanol.

4. The method of claim 1, wherein the lipids comprise phospholipids.

5. The method of claim 4, wherein the phospholipids and the solvent are combined at a concentration of about 400 mg to 800 mg phospholipids per 1 ml of solvent.

6. The method of claim 4, wherein the phospholipids and the solvent are combined at a concentration of about 500 mg to 700 mg phospholipids per 1 ml of solvent.

7. The method of claim 4, wherein the phospholipids and the solvent are combined at a concentration of about 550 mg to 650 mg phospholipids per 1 ml of solvent.

8. The method of claim 5, wherein the lipids further comprise cholesterol.

9. The method of any of claim 8, wherein the cholesterol and the solvent are combined at a concentration of about 50 mg to 250 mg cholesterol per 1 ml of solvent.

10. The method of any of claim 8, wherein the cholesterol and the solvent are combined at a concentration of about 100 mg to 200 mg cholesterol per 1 ml of solvent.

11. The method of claim 8, wherein the cholesterol and the solvent are combined at a concentration of about 125 mg to 175 mg cholesterol per 1 ml of solvent.

12. The method of claim 1 wherein the dissolving comprises warming the lipids and solvent to 40 to 85° C.

13. The method of claim 12 comprising warming the aqueous solution comprising an encapsulant dissolved therein to 40 to 85° C. prior to addition to the lipid solution.

14. The method of claim 1, wherein the lipids and solvent are dissolved in a vessel to provide a dissolved lipid composition and the aqueous solution comprising an encapsulant dissolved therein is injected into the vessel containing the dissolved lipid composition.

15. The method of claim 13, further comprising cooling the liposomes to a temperature that is below the phase transition temperature of the lipids.

16. The method of claim 1, wherein the aqueous solution is selected from the group consisting of an acidic solution and a basic solution.

17. The method of claim 1, wherein the encapsulant is a salt.

18. The method of claim 17, wherein the salt is a weak base salt selected from the group consisting of a sulfate salt an eprodisate salt and an edisylate salt.

19. The method of claim 18 wherein adding the weak base salt to the lipid solution comprises adding a first volume of the weak base salt to the lipid solution followed by adding a second volume of the weak base salt to the lipid solution.

20. The method of claim 19 wherein the ratio of the first volume to the second volume is 5:1 to 1:5.

21. The method of claim 1, wherein the encapsulant is selected from the group consisting of a chemical bioactive agent and a biologic bioactive agent.

22. The method of claim 21, wherein the chemical bioactive agent is an analgesic.

23. The method of claim 1, further comprising diluting the liposomes in an aqueous solution.

24. The method of claim 1, further comprising washing the liposomes to remove liposome loading agent or encapsulant from the extraliposomal space.

\* \* \* \* \*